United States Patent
Mariani et al.

(10) Patent No.: US 10,626,473 B2
(45) Date of Patent: Apr. 21, 2020

(54) METHODS AND COMPOSITIONS FOR DETECTING ZIKA VIRUS

(71) Applicant: Genetics & IVF Institute, Fairfax, VA (US)

(72) Inventors: Brian D. Mariani, Fairfax, VA (US); Harvey J. Stern, Fairfax, VA (US)

(73) Assignee: Genetics & IVG Institute, Inc., Farifax, VA (US)

( * ) Notice: Subject to any disclaimer, the term of this patent is extended or adjusted under 35 U.S.C. 154(b) by 43 days.

(21) Appl. No.: 15/723,337

(22) Filed: Oct. 3, 2017

(65) Prior Publication Data
US 2018/0142310 A1 May 24, 2018

Related U.S. Application Data

(60) Provisional application No. 62/403,303, filed on Oct. 3, 2016.

(51) Int. Cl.
*C07H 21/04* (2006.01)
*C12Q 1/68* (2018.01)
*C12Q 1/70* (2006.01)

(52) U.S. Cl.
CPC ......... *C12Q 1/701* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS 6,593,086 B2 * 7/2003 Zhang .................... C12Q 1/682 435/6.1
2019/0264294 A1 * 8/2019 Koppelman ............. C12Q 1/70

FOREIGN PATENT DOCUMENTS

WO 2017040316 A1 3/2017

OTHER PUBLICATIONS

Balm et al. (J. of Medical Virology, vol. 84, pp. 1501-1505, 2012 (Year: 2012).*
Huits (Kinetics of Zika virus persistence in semen, Bull World Health Organ. E-pub: Jul. 6, 2016. Doi: http://dx.doi.org/10.2471/BLT.16.181370 (Year: 2016).*
Faye et al (Virology Journal, vol. 10, No. 311, pp. 1-8, 2013 (Year: 2013).*
Barzon et al., "Infection dynamics in a traveller with persistent shedding of Zika virus RNA in semen for six months after returning from Haiti to Italy, Jan. 2016," Eurosurveillance, Aug. 11, 2016; vol. 21, issue 32.
Brooks et al., "Likely Sexual Transmission of Zika Virus from a Man with No Symptoms of Infection—Maryland, 2016," Morbidity and Mortality Weekly Report, Sep. 2, 2016; vol. 65, No. 34, pp. 915-916.
Cugola et al., "The Brazilian Zika Virus Strain Causes Birth Defects in Experimental Models," Nature, Jun. 9, 2016; vol. 534, issue 7606, pp. 267-271.
D'Ortenzio et al., "Evidence of Sexual Transmission of Zika Virus," The New England Journal of Medicine, Jun. 2, 2016; vol. 374, No. 22, pp. 2195-2198.
Fréour et al., "Sexual transmission of Zika virus in an entirely asymptomatic couple returning from a Zika epidemic area, France, Apr. 2016," Eurosurveillance, Jun. 9, 2016; vol. 21, issue 23.
Mansuy et al., "Zika virus: high infectious viral load in semen, a new sexually transmitted pathogen?," The Lancet Infectious Diseases, Apr. 1, 2016; vol. 16, issue 4, p. 405.
Metsky et al., "Zika virus evolution and spread in the Americas," Nature, Jun. 15, 2017; vol. 546, issue 7658, pp. 411-415.
Musso et al., "Potential Sexual Transmission of Zika Virus," Emerging Infectious Diseases, Feb. 2015; vol. 21, No. 2, pp. 359-361.
Musso et al., "Zika Virus," Clinical Microbiology Reviews, Jul. 2016; vol. 29, No. 3, pp. 487-524.
Smith et al., "Comparison of Biosequences," Advances in Applied Mathematics, Dec. 1981; vol. 2, issue 4, pp. 482-489.
"Zika virus strain PRVABC59, complete genome," GeneBank Accession No. KU501215, available at www.ncbi.nlm.nih.gov/nuccore/KU501215.

* cited by examiner

*Primary Examiner* — Jeanine A Goldberg
(74) *Attorney, Agent, or Firm* — Greenberg Traurig, LLP; Fang Xie

(57) ABSTRACT

Provided herein is a highly sensitive and robust method for Zika detection in semen, as well as related compositions. The method can include: (a) extracting nucleic acids from a human semen sample; (b) detecting Zika virus nonstructural protein 5 (NS5) mRNA using real-time reverse-transcription polymerase chain reaction (rRT-PCR); and (c) simultaneously, in the rRT-PCR, detecting human beta-actin mRNA as positive control.

13 Claims, No Drawings
Specification includes a Sequence Listing.

SEQUENCE LISTING

```
<160> NUMBER OF SEQ ID NOS: 27

<210> SEQ ID NO 1
<211> LENGTH: 20
<212> TYPE: DNA
<213> ORGANISM: Zika virus

<400> SEQUENCE: 1
caaaacaaag tggtaaaggt                                                   20

<210> SEQ ID NO 2
<211> LENGTH: 20
<212> TYPE: DNA
<213> ORGANISM: Zika virus

<400> SEQUENCE: 2
cttgtctcga aataatgtcc                                                   20

<210> SEQ ID NO 3
<211> LENGTH: 23
<212> TYPE: DNA
<213> ORGANISM: Zika virus

<400> SEQUENCE: 3
cttagaccag ctgaaaaagg gaa                                               23

<210> SEQ ID NO 4
<211> LENGTH: 17
<212> TYPE: DNA
<213> ORGANISM: Zika virus

<400> SEQUENCE: 4
cttgaacgag gatcact                                                      17

<210> SEQ ID NO 5
<211> LENGTH: 20
<212> TYPE: DNA
<213> ORGANISM: Zika virus
```

```
<400> SEQUENCE: 5
ctcttctagg acatatccga                                              20

<210> SEQ ID NO 6
<211> LENGTH: 18
<212> TYPE: DNA
<213> ORGANISM: Zika virus

<400> SEQUENCE: 6
tcccagccct tcaacacc                                                18

<210> SEQ ID NO 7
<211> LENGTH: 17
<212> TYPE: DNA
<213> ORGANISM: Homo sapiens

<400> SEQUENCE: 7
cgcgctcgtc gtcgaca                                                 17

<210> SEQ ID NO 8
<211> LENGTH: 18
<212> TYPE: DNA
<213> ORGANISM: Homo sapiens

<400> SEQUENCE: 8
ccaccatcac gccctggt                                                18

<210> SEQ ID NO 9
<211> LENGTH: 19
<212> TYPE: DNA
<213> ORGANISM: Homo sapiens

<400> SEQUENCE: 9
acggctccgg catgtgcaa                                               19

<210> SEQ ID NO 10
<211> LENGTH: 18
<212> TYPE: DNA
<213> ORGANISM: Cytomegalovirus

<400> SEQUENCE: 10
cggtggccaa agtgtagg                                                18

<210> SEQ ID NO 11
<211> LENGTH: 21
<212> TYPE: DNA
<213> ORGANISM: Cytomegalovirus

<400> SEQUENCE: 11
aaggtctttg cccagtacat t                                            21

<210> SEQ ID NO 12
<211> LENGTH: 24
<212> TYPE: DNA
<213> ORGANISM: Cytomegalovirus

<400> SEQUENCE: 12
ctcatctgac tcctcggcga tggc                                         24

<210> SEQ ID NO 13
<211> LENGTH: 20
<212> TYPE: DNA
```

<213> ORGANISM: Herpes Simplex Virus type 1 (HSV-1)

<400> SEQUENCE: 13
ataccgacca caccgacgaa                                           20

<210> SEQ ID NO 14
<211> LENGTH: 23
<212> TYPE: DNA
<213> ORGANISM: Herpes Simplex Virus type 1 (HSV-1)

<400> SEQUENCE: 14
acgcaccaca caaaagagac ctt                                       23

<210> SEQ ID NO 15
<211> LENGTH: 23
<212> TYPE: DNA
<213> ORGANISM: Herpes Simplex Virus type 1 (HSV-1)

<400> SEQUENCE: 15
cttcagcgcg aacgaccaac tac                                       23

<210> SEQ ID NO 16
<211> LENGTH: 18
<212> TYPE: DNA
<213> ORGANISM: Herpes Simplex Virus type 2 (HSV-2)

<400> SEQUENCE: 16
cggggtcggt gtggtgtt                                             18

<210> SEQ ID NO 17
<211> LENGTH: 18
<212> TYPE: DNA
<213> ORGANISM: Herpes Simplex Virus type 2 (HSV-2)

<400> SEQUENCE: 17
tgccgtgata cgcgatgc                                             18

<210> SEQ ID NO 18
<211> LENGTH: 23
<212> TYPE: DNA
<213> ORGANISM: Herpes Simplex Virus type 2 (HSV-2)

<400> SEQUENCE: 18
cgttcgcaat gcagcttatg acc                                       23

<210> SEQ ID NO 19
<211> LENGTH: 25
<212> TYPE: DNA
<213> ORGANISM: Human Papillomavirus type 16 (HPV-16)

<400> SEQUENCE: 19
agaaccggac agagcccatt acaat                                     25

<210> SEQ ID NO 20
<211> LENGTH: 26
<212> TYPE: DNA
<213> ORGANISM: Human Papillomavirus type 16 (HPV-16)

<400> SEQUENCE: 20
ttcctagtgt gcccattaac aggtct                                    26

<210> SEQ ID NO 21
<211> LENGTH: 29

```
<212> TYPE: DNA
<213> ORGANISM: Human Papillomavirus type 16 (HPV-16)

<400> SEQUENCE: 21
acgcttcggt tgtgcgtaca aagcacaca                                    29

<210> SEQ ID NO 22
<211> LENGTH: 25
<212> TYPE: DNA
<213> ORGANISM: Human Papillomavirus type 18 (HPV-18)

<400> SEQUENCE: 22
caacatagct gggcactata gaggc                                        25

<210> SEQ ID NO 23
<211> LENGTH: 32
<212> TYPE: DNA
<213> ORGANISM: Human Papillomavirus type 18 (HPV-18)

<400> SEQUENCE: 23
gacatagaag gtcaaccgga atttcatttt gg                                32

<210> SEQ ID NO 24
<211> LENGTH: 27
<212> TYPE: DNA
<213> ORGANISM: Human Papillomavirus type 18 (HPV-18)

<400> SEQUENCE: 24
accgagcacg acaggaacga ctccaac                                      27

<210> SEQ ID NO 25
<211> LENGTH: 23
<212> TYPE: DNA
<213> ORGANISM: Homo sapiens

<400> SEQUENCE: 25
ccagagcata aggccaccgg tat                                          23

<210> SEQ ID NO 26
<211> LENGTH: 22
<212> TYPE: DNA
<213> ORGANISM: Homo sapiens

<400> SEQUENCE: 26
atccacccat gggctcgtaa cc                                           22

<210> SEQ ID NO 27
<211> LENGTH: 24
<212> TYPE: DNA
<213> ORGANISM: Homo sapiens

<400> SEQUENCE: 27
tcacctgagc caatggtaaa cctg                                         24
```

METHODS AND COMPOSITIONS FOR DETECTING ZIKA VIRUS

CROSS-REFERENCE TO RELATED APPLICATIONS

This application claims priority to and the benefit of U.S. Provisional Patent Application No. 62/403,303 filed Oct. 3, 2016, the entire disclosure of which is incorporated herein by reference.

SEQUENCE LISTING

The ASCII text file submitted on Feb. 8, 2018 via EFS-Web, entitled "020001SEQ_Listing.txt" created on Feb. 8, 2018, having a size of 4,571 bytes, is incorporated herein by reference in its entirety.

FIELD

The present disclosure relates to methods and compositions for detecting the Zika virus in semen samples.

BACKGROUND

Zika virus (ZIKV) is an emerging mosquito-borne pathogen (family Flaviviridae, genus *Flavivirus*), believed to be transmitted to humans by infected *Aedes* spp. mosquitoes. Recent studies have demonstrated that ZIKV is endemic to Africa and Southeast Asia, causing significant health concern globally. In May 2015, the Pan American Health Organization (PAHO) issued an alert regarding the first confirmed ZIKV infection in Brazil. On Feb. 1, 2016, the World Health Organization (WHO) declared ZIKV a Public Health Emergency of International Concern (PHEIC) regarding a recent cluster of microcephaly cases and other neurological disorders and the possible association of these illnesses with ZIKV infections.

As many as four million people could be infected by the end of 2016. About 1 in 5 people infected with ZIKV become ill (i.e., develop Zika). ZIKV infection is characterized by mild fever (37.8° C.-38.5° C.); arthralgia, notably of small joints of hands and feet; myalgia, headache; retroorbital pain; conjunctivitis; and cutaneous maculopapular rash. ZIKV infection is believed to be asymptomatic or mildly symptomatic in most cases. Thus, Zika can be misdiagnosed during the acute (viremic) phase because of nonspecific influenza-like signs and symptoms. Hemorrhagic signs have not been reported in ZIKV-infected patients. However neurologic complications, including Guillain-Barré syndrome, have been observed. Recent data also show that the Brazilian ZIKV ($ZIKV^{BR}$) strain infects fetuses and causes birth defects including microcephaly (*Nature* 534, 267-271 (9 Jun. 2016)).

Diagnosis of Zika fever requires virus isolation and serology, which are time consuming or cross-reactive, and make rapid serologic confirmation difficult. Thus, improved technology for rapid, sensitive detection of Zika is urgently needed.

ZIKV is additionally unique among the flaviviruses in that it is known to be transmissible by men to their sexual partners via infection of semen. ZIKV is found in semen for a longer period of time than in blood, urine, saliva or other tissues samples. Several case reports exist where men transmitted Zika to their sexual partners after returning from an area of active viral transmission (Evidence of Sexual Transmission of Zika Virus. D'Ortenzio E, Matheron S, Yazdanpanah Y. N Engl J Med 2016; 374:2195-2198, Jun. 2, 2016). In these cases, the partner had no travel history in an affected area. At the current time, information regarding the duration of Zika shedding in semen and the infectivity of different viral loads is scant or absent. A recent report from France noted a viral load of $1 \times 10^{8.6}$ copies/mL in semen of a patient returning from Brazil (Zika virus: high infectious viral load in semen, a new sexually transmitted pathogen? Mansuy, J M, Dutertre, M, Mengelle, C et al. *Lancet Infect Dis.* 2016; 16: 405).

It is now documented that Zika is retained in semen for over 6 months (Barzon L, et al., Infection dynamics in a traveller with persistent shedding of Zika virus RNA in semen for six months after returning from Haiti to Italy, January 2016. Euro Surveill. 2016; 21(32)). This underscores the need for a semen-based diagnostic assay for Zika. Recent reports separately document the transmission of the virus from an asymptomatic male to their sexual partner (Brooks R B et al., Likely Sexual Transmission of Zika Virus from a Man with No Symptoms of Infection—Maryland, 2016. MMWR Morb Mortal Wkly Rep 2016; 65:915-916; Fréour T et al., Sexual transmission of Zika virus in an entirely asymptomatic couple returning from a Zika epidemic area, France, April 2016. Euro Surveill. 2016; 21(23)). In these cases, the male may not realize they are carriers of the virus in the absence of normal symptoms. Additional review of Zika virus can be found in "Zika virus," Musso D, Gubler D J. 2016. Clin Microbiol Rev 29:487-524.

One of the barriers to the development of diagnostic tests using sperm is the difficulty in working with this sample type. Thus, an urgent need exists for a highly sensitive and robust assay for Zika detection in semen.

SUMMARY

In one aspect, a highly sensitive and robust method for Zika detection in semen is provided. The method can include: (a) extracting nucleic acids from a human semen sample; (b) detecting Zika virus nonstructural protein 5 (NS5) mRNA using real-time reverse-transcription polymerase chain reaction (rRT-PCR); and (c) simultaneously, in the rRT-PCR, detecting human beta-actin mRNA as positive control. It should be noted that while human beta-actin mRNA is used as an exemplary control, other universally expressed mRNA (e.g., of housekeeping genes) such as those of aldolase, dihydropholate reductase, glyceraldehyde phosphate dehydrogenase, histone 3.3 and hypoxanthine phosphoribosyltransferase can also be used.

In some embodiments, the nucleic acids are RNA where substantially all DNA has been removed. The nucleic acids can also be a mixture of RNA and DNA.

In various embodiments, the human semen sample can be fresh, refrigerated, frozen or cryopreserved which have all been shown to work well in the methods disclosed herein.

In some embodiments, step (b) comprises detecting a 73-nucleotide region from g.9389 to g.9461 of GeneBank Accession No. KU501215. To that end, the method can further include providing: a forward primer that is 15-25 nucleotides long and targets a region located within g.9389 to g.9414 of GeneBank Accession No. KU501215; a reverse primer that is 15-25 nucleotides long and targets a region located within g.9436 to g.9461 of GeneBank Accession No. KU501215; and a TAQMAN® probe that is 18-30 nucleotides long and targets a region located within g.9404 to g.9446 of GeneBank Accession No. KU501215. In one example, the forward primer, the reverse primer and the probe have the nucleic acid sequences of SEQ ID NOs: 1, 2 and 3, respectively.

In some embodiments, step (b) comprises detecting a 91-nucleotide region from g.9142 to g.9232 of GeneBank Accession No. KU501215. Exemplary primers and probes include: a forward primer that is 15-25 nucleotides long and targets a region located within g.9142 to g.9167 of GeneBank Accession No. KU501215; a reverse primer that is 15-25 nucleotides long and targets a region located within g.9207 to g.9232 of GeneBank Accession No. KU501215; and a TAQMAN® probe that is 18-30 nucleotides long and targets a region located within g.9157 to g.9217 of GeneBank Accession No. KU501215. For example, the forward primer, the reverse primer and the probe can have the nucleic acid sequences of SEQ ID NOs: 4, 5 and 6, respectively.

In some embodiments, step (c) comprises using a forward primer, a reverse primer and a TAQMAN® probe having the nucleic acid sequences of SEQ ID NOs: 7, 8 and 9, respectively, for detecting the human beta-actin mRNA.

A second aspect relates to a composition for detecting Zika virus, comprising: a forward primer that is 15-25 nucleotides long and targets a region located within g.9389 to g.9414 or g.9142 to g.9167 of GeneBank Accession No. KU501215; a reverse primer that is 15-25 nucleotides long and targets a region located within g.9436 to g.9461 or g.9207 to g.9232 of GeneBank Accession No. KU501215; and a TAQMAN® probe that is 18-30 nucleotides long and targets a region located within g.9404 to g.9446 or g.9157 to g.9217 of GeneBank Accession No. KU501215. In some embodiments, the forward primer can have the nucleic acid sequence of SEQ ID NO: 1 or 4, the reverse primer can have the nucleic acid sequence of SEQ ID NO: 2 or 5, and the probe can have the nucleic acid sequence of SEQ ID NO: 3 or 6.

A further aspect relates to a method for detecting two or more viruses, comprising: (a) extracting nucleic acids from a human semen sample; (b) subjecting a first portion of the nucleic acids to real-time reverse-transcription polymerase chain reaction (rRT-PCR) for detecting Zika virus nonstructural protein 5 (N55) mRNA, while simultaneously, in the rRT-PCR, detecting human beta-actin mRNA as a first positive control; and (c) subjecting a second portion of the nucleic acids to real-time PCR for detecting one or more DNA viruses, while simultaneously, in the real-time PCR, detecting human Amelogenin gene as a second positive control. In some embodiments, the nucleic acids are a mixture of RNA and DNA. It should be noted that while human Amelogenin gene is used as an exemplary control, other genomic DNA (e.g., Y chromosome genes) can also be used.

In various embodiments, step (b) comprises detecting a 73-nucleotide region from g.9389 to g.9461 or a 91-nucleotide region from g.9142 to g.9232 of GeneBank Accession No. KU501215. Suitable primers and probes can include: a forward primer that is 15-25 nucleotides long and targets a region located within g.9389 to g.9414 or g.9142 to g.9167 of GeneBank Accession No. KU501215; a reverse primer that is 15-25 nucleotides long and targets a region located within g.9436 to g.9461 or g.9207 to g.9232 of GeneBank Accession No. KU501215; and a TAQMAN® probe that is 18-30 nucleotides long and targets a region located within g.9404 to g.9446 or g.9157 to g.9217 of GeneBank Accession No. KU501215. For example, the forward primer can have the nucleic acid sequence of SEQ ID NO: 1 or 4, the reverse primer can have the nucleic acid sequence of SEQ ID NO: 2 or 5, and the probe can have the nucleic acid sequence of SEQ ID NO: 3 or 6.

In certain embodiments, the one or more DNA viruses are selected from cytomegalovirus (CMV), herpes simplex virus (HSV) 1 & 2, and human papillomavirus (HPV) strains 16 & 18. In some embodiments, the method can further include providing: a forward primer, a reverse primer and a TAQMAN® probe having the nucleic acid sequences of SEQ ID NOs: 10, 11 and 12, respectively, for detecting CMV; a forward primer, a reverse primer and a TAQMAN® probe having the nucleic acid sequences of SEQ ID NOs: 13, 14 and 15, respectively, for detecting HSV 1; a forward primer, a reverse primer and a TAQMAN® probe having the nucleic acid sequences of SEQ ID NOs: 16, 17 and 18, respectively, for detecting HSV 2; a forward primer, a reverse primer and a TAQMAN® probe having the nucleic acid sequences of SEQ ID NOs: 19, 20 and 21, respectively, for detecting HPV 16; and/or a forward primer, a reverse primer and a TAQMAN® probe having the nucleic acid sequences of SEQ ID NOs: 22, 23 and 24, respectively, for detecting HPV 18.

In some embodiments, step (c) comprises using a forward primer, a reverse primer and a TAQMAN® probe having the nucleic acid sequences of SEQ ID NOs: 25, 26 and 27, respectively, for detecting the human Amelogenin gene.

DETAILED DESCRIPTION

Provided herein, in one aspect, is a highly sensitive and robust real-time reverse-transcription PCR (rRT-PCR) assay (also referred to herein as "GIVF-ZIKV Assay") as well as related kits and compositions for Zika detection in semen. In some embodiments, the assay is optimized for detection of current Brazilian strains.

The assay can include extracting RNA from a semen sample, and detecting the Zika virus NS5 mRNA using real-time reverse-transcription PCR, while simultaneously detecting beta-actin mRNA as internal positive control. It should be noted that while human beta-actin mRNA is used as an exemplary control, other universally expressed mRNA (e.g., of housekeeping genes) such as those of aldolase, dihydropholate reductase, glyceraldehyde phosphate dehydrogenase, histone 3.3 and hypoxanthine phosphoribosyltransferase can also be used.

In some embodiments, a 73-nucleotide region (from g.9389 to g.9461 within GeneBank Accession No. KU501215, available at www.ncbi.nlm.nih.gov/nuccore/KU501215) or 91-nucleotide region (from g.9142 to g.9232 within GeneBank Accession No. KU501215) is detected for the Zika virus NS5 mRNA. Specific primers and probes (e.g., TAQMAN® probe) for use in the real-time reverse-transcription PCR are also provided herein. The TAQMAN® probe can have a reporter dye (e.g., FAM) attached at one end and a quencher (e.g., BHQ) attached at the other end.

For example, a forward primer for the 73-nucleotide region can be 15-25 nucleotides long and located within g.9389 to g.9414 of GeneBank Accession No. KU501215. A reverse primer for the 73-nucleotide region can be 15-25 nucleotides long and located within g.9436 to g.9461 of GeneBank Accession No. KU501215. A TAQMAN® probe for the 73-nucleotide region can be 18-30 nucleotides long and located within g.9404 to g.9446 of GeneBank Accession No. KU501215. In one embodiment, the forward primer, reverse primer and probe can have the sequences of SEQ ID NOs: 1, 2 and 3, respectively.

In some embodiments, a forward primer for the 91-nucleotide region can be 15-25 nucleotides long and located within g.9142 to g.9167 of GeneBank Accession No. KU501215. A reverse primer for the 91-nucleotide region can be 15-25 nucleotides long and located within g.9207 to g.9232 of GeneBank Accession No. KU501215. A TAQ-MAN® probe for the 91-nucleotide region can be 18-30 nucleotides long and located within g.9157 to g.9217 of GeneBank Accession No. KU501215. In one embodiment, the forward primer, reverse primer and probe can have the sequences of SEQ ID NOs: 4, 5 and 6, respectively.

In various embodiments, the Zika virus assay disclosed herein can be used for the qualitative detection of RNA from the Zika virus in human semen from patients at risk of exposure to Zika virus or with signs and symptoms of Zika virus infection in conjunction with appropriate epidemiological factors to aid in the presumptive diagnosis of Zika virus infection. It is important to note that the viral titers in semen are significantly higher in the semen reservoir compared to the titers found in blood or urine. A more recent report from Italy as shown that Zika virus remained in the semen of an infected male for over 6 months. This situation highlights the need for a sensitive and accurate detection method for identifying individuals (males) who harbor and maintain the virus in semen to prevent the transmission of Zika to sexual partners.

Data on clearance of viral particles from the male reproductive tract is obviously essential in making recommendations on the management of the male exposed to, or infected with Zika virus. The implications of these questions will have a profound effect on couples planning to become pregnant by either natural conception or assisted reproduction. The Zika test disclosed herein can be used by men infected with Zika who wish to be assured that they are not shedding virus in their semen prior to attempting conception. Likewise, men exposed to Zika but without symptoms can utilize a diagnostic test to confirm that their semen is free of Zika. Finally, for couples using assisted reproductive technologies, the Zika assay disclosed herein can be used to assure couples of the safety of the semen prior to undertaking a complicated and expensive medical procedure.

Results obtained using the methods and compositions disclosed herein can be used for the presumptive identification of Zika virus and should be managed in consultation with public health or other authorities to whom reporting is required, such as the Center for Disease Control of the United States. The diagnosis of Zika virus infection must be made based on history, signs, symptoms, exposure likelihood and other laboratory evidence in addition to the identification Zika virus.

In another aspect, the Zika assay disclosed herein can be added to existing semen testing programs utilized to exclude from donation semen those containing various pathogens such as herpes simplex virus (HSV) 1 & 2, cytomegalovirus (CMV), and human papillomavirus (HPV) (e.g., strains 16 & 18). Extraction methods can be used that yields intact RNA and DNA in order to test for DNA viruses (e.g., CMV, HSV, HPV) and the RNA-based Zika virus as part of a semen-specific panel, including appropriate internal positive controls. In this manner, a comprehensive assay of critical importance can be utilized that is above and beyond the standard blood-based FDA regulations to reduce or eliminate the potential of transmitting harmful pathogenic agents to recipients of infected semen in situations where standard protocols failed to directly interrogate the final product: the semen itself.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

As used herein, "including," "comprising," "having," "containing," "involving," and variations thereof herein, are meant to encompass the items listed thereafter and equivalents thereof as well as additional items. "Consisting of" shall be understood as a close-ended relating to a limited range of elements or features. "Consisting essentially of" limits the scope to the specified elements or steps but does not exclude those that do not materially affect the basic and novel characteristics of the claimed invention.

The term "gene" refers to a nucleic acid (e.g., DNA or RNA) sequence that comprises coding sequences necessary for the production of an RNA or a polypeptide or its precursor. The term "portion" when used in reference to a gene refers to fragments of that gene. The fragments may range in size from a few nucleotides to the entire gene sequence minus one nucleotide. The term "gene" also encompasses the coding regions of a structural gene and includes sequences located adjacent to the coding region on the 5' and/or 3' ends such that the gene corresponds to the length of the full-length mRNA. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "primer" refers to an oligonucleotide that acts as a point of initiation of DNA synthesis in a PCR reaction. A primer is usually about 15 to about 40 nucleotides in length (or shorter or longer) and typically includes at least one target-hybridized region that is at least substantially complementary to the target sequence.

The term "probe" refers to an oligonucleotide that hybridizes to a target sequence on a target nucleic acid. Target sequence refers to a region of nucleic acid that is to be analyzed and comprises the polymorphic site of interest. For TAQMAN® assays, the probe can additionally contain a quencher and a dye (e.g., fluorescent). When the probes are intact, fluorescence is suppressed because the quencher dyes are in the proximity of the reporter dyes. At least two probes can be included in one TAQMAN® assay; one for the major allele, and the other for the minor allele in a two-allele system. More probes can be included if there are more than two alleles within the target region.

The term "TAQMAN®" is a technology that exploits the 5'-3' nuclease activity of Taq DNA polymerase to allow direct detection of the PCR product by the release of a fluorescent report from a probe as a result of PCR. In the PCR annealing step, the probes hybridize to the targeted site. During PCR extension, the reporter and quencher dyes are released due to the 5' nuclease activity of the Taq polymerase, resulting in an increased characteristic fluorescence of the reporter dye. Exonuclease activity only happens on the perfectly hybridized probes, since a probe containing a mismatched base will not be recognized by the Taq polymerase. "Taq polymerase" refers to a heat stable enzyme used in the polymerase chain reaction (PCR) to amplify target DNA. It was discovered in bacterium Thermus aquaticus and hence the name. It should be noted that other polymerases having 5'-3' nuclease activity can also be used to replace the Taq polymerase in TAQMAN® assays.

The term "nucleic acid" refers to polymers of nucleotides (e.g., ribonucleotides or deoxyribonucleotides) both natural and non-natural. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Nucleic acids may include naturally occurring bases (adenosine, guanidine, cytosine, uracil and thymidine) as well as non-natural bases.

The GeneBank accession numbers provided throughout this description are derived from the NCBI database (National Ceter for Biotechnology Information) maintained by the National Institute of Health, USA.

Conventional molecular biology, microbiology, and recombinant DNA techniques including sequencing techniques are well known among those skilled in the art. Such techniques are explained fully in the literature, See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al. 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames &. S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F, M. Ausubel, et al. (eds), Current Protocols in Molecular Biology, John Wiley & Sons, Inc. (1994).

Other terms used in the fields of recombinant nucleic acid technology and molecular and cell biology as used herein will be generally understood by one of ordinary skill in the applicable arts.

Real-Time RT-PCR Assay for Zika Virus

GIVF-ZIKV Assay is a multiplex real-time reverse transcription polymerase chain reaction (rRT-PCR) test. Real-time Polymerase Chain Reaction (PCR) is the ability to monitor the progress of the PCR as it occurs (i.e., in real time). Data is therefore collected throughout the PCR process, rather than at the end of the PCR. In real-time PCR, reactions are characterized by the point in time during cycling when amplification of a target is first detected rather than the amount of target accumulated after a fixed number of cycles. The higher the starting copy number of the nucleic add target, the sooner a significant increase in fluorescence is observed.

Generally, two types of chemistries can be used to detect PCR products—TaqMan® chemistry or SYBR™ Green dye chemistry. In TaqMan® chemistry, one may utilize an oligonucleotide probe labeled with a reporter dye (e.g., fluorescent such as FAM or VIC) at the 5' end of the probe and a quencher dye (e.g., nonfluorescent quencher) at the 3' end of the probe. The proximity of the quencher to the intact probe maintains a low fluorescence for the reporter. During the PCR reaction, the 5' nuclease activity of DNA polymerase cleaves the probe, and separates the dye and quencher, resulting in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target sequence position and hybridize to the nucleic acid molecule only if a particular sequence is present.

Genotyping is performed using oligonucleotide primers and probes. Oligonucleotides may be synthesized and prepared by any suitable methods (such as chemical synthesis), which are known in the art. Oligonucleotides may also be conveniently available through commercial sources. One of the skilled artisans would easily optimize and identify primers flanking the gene of interest in a PCR reaction. Commercially available primers may be used to amplify a particular gene of interest for a particular sequence. A number of computer programs (e.g., Primer-Express) are readily available to design optimal primer probe sets. It will be apparent to one of skill in the art that the primers and probes based on the nucleic acid information provided (or publically available with accession numbers) can be prepared accordingly.

Methods for labeling of probes are known in the art. The labeled probes are used to hybridize within the amplified region during the amplification region. The probes are modified so as to avoid them from acting as primers for amplification. The detection probe is labeled with two dyes, one capable of quenching the fluorescence of the other dye when in proximity. One dye is attached to the 5' terminus of the probe and the other is attached to an internal site or the 3' terminus, so that quenching occurs when the probe is in a hybridized state.

Primers and probes can be designed based on the target sequence. Algorithms for designing primers and probes are widely used and readily available in the art (e.g., Primer-BLAST available at www.ncbi.nlm.nih.gov/tools/primer-blast/). In essence any primer(s) suitable for amplifying a target sequence in a polymerase chain reaction can be used. In some embodiments it may be desirable to keep maximum amplicon size under 400 bp (e.g., 50-150 bp). The probe(s) should be designed to target a region flanked by the forward and reverse primer pair, with suitable length (e.g., 18-22 bases but can be longer or shorter) and proper dye labeling as discussed herein.

In addition, one of ordinary skill in the art of design of primers will recognize that a given primer need not hybridize with 100% complementarity to prime the synthesis of a complementary nucleic acid strand. Primer pair sequences may be a "best fit" amongst several aligned sequences, thus they need not be fully complementary to the hybridization region of any one of the sequences in the alignment. Moreover, a primer may hybridize over one or more segments such that intervening or adjacent segments are not involved in the hybridization event (e.g., for example, a loop structure or a hairpin structure). The primers may comprise at least 70%, at least 75%, at least 80%, at least 85%, at least 90%, at least 95% or at least 99% sequence identity with a target nucleic acid of interest. Thus, in some embodiments, an extent of variation of 70% to 100%, or any range falling within, of the sequence identity is possible relative to the specific primer sequences disclosed herein.

To illustrate, determination of sequence identity is described in the following example. A primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of target nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%. In some embodiments, the primers used herein comprise at least 70%, at least 75%, at least 80%, at least 85%, at least 90%, at least 92%, at least 94%, at least 95%, at least 96%, at least 98%, or at least 99%, or 100% (or any range falling within) sequence identity with the primer sequences specifically disclosed herein.

In some embodiments, the Zika virus primer and probe sets disclosed herein are designed to detect RNA from the Zika virus in semen from male patients presenting with signs and symptoms of the Zika virus infection, or with known exposure to Zika virus, in conjunction with epidemiological risk factors whose sexual partner(s) is (are) pregnant or able to become pregnant. The assay primer/probe set has been optimized for the current Brazilian strains of ZIKV (isolated in the Americas) with low cross-over with other related viruses such as Dengue, Yellow fever, West Nile and Chikungunya virus.

GIVF-ZIKV has been validated for the detection of Zika viral RNA extracted from whole, washed and cryopreserved semen. Data limited to the testing of whole (raw) and washed semen will be present herein. Nucleic acids are isolated and purified from semen protocols that yield either DNA-free RNA or a combination of intact, full-length RNA and DNA. The latter method is used for the simultaneous detection of DNA-based and RNA-based pathogens in the same specimen. Data using both nucleic acid extraction protocols is presented below, as both methods gave equal Ct values for positive controls and viral detection for contrived positive samples run in parallel.

In some embodiments, the purified RNA is converted to cDNA via a reverse transcriptase, which is then subsequently amplified via PCR in a real-time thermal cycler using Taq polymerase. In the process as PCR amplicon is generated, the probe anneals to a specific target sequence located between the forward and reverse primers. During the extension phase of the PCR cycle, the 5' nuclease activity of Taq polymerase degrades the probe, physically releasing the 5' reporter dye from the 3' quencher dye, generating a fluorescent signal. With each cycle, additional reporter dye molecules are cleaved from their respective probes, increasing the fluorescence intensity.

Fluorescence intensity is monitored at each PCR cycle using preset excitation and emission wavelength windows for each fluorochrome. Since two sequences (viral and patient-derived) are targeted in this single tube multiplex format, two flourochromes are employed that yield signals of distinct emission wavelength allowing detection of 1) Zika target (e.g., FAM), and 2) patient-derived (e.g., ACTB mRNA) internal positive control (e.g., TET). The detection of fluorescence is cumulative; with each successive cycle, the amount of signal detected is proportional to the amount of target amplicon generated at each cycle point. With the inclusion of the patient-derived internal positive control, detection of the internal positive control (e.g., ACTB mRNA) signal must be positive before any determination of the presence or absence of virus can be made.

The assay detects, in some embodiments, a region of the Zika virus nonstructural protein 5 (NS5) gene. Zika virus strain PRVABC59 (GenBank Accession No.: KU501215.1) isolated in Puerto Rico (2016) and posted on GenBank on Feb. 1, 2016 by the Diagnostic & Reference Laboratory, Arbovirus Diseases Branch, Centers for Disease Control & Prevention, Fort Collins, Colo., was used as sequence reference and wet-work testing. Live virus stock, purified viral RNA from this strain, or a 118-nucleotide synthetic RNA encompassing the targeted region of the NS5 gene was used as template for validation studies. The single stranded 118-nucleotide synthetic RNA extends from position g.9366 to g.9484 of KU501215.

In one embodiment, a 73-nucleotide amplicon from the Zika virus NS5 gene is detected, the genomic position of which extends from nucleotide g.9389 to nucleotide g.9461 within KU501215. In another embodiment, a 91-nucleotide amplicon (from g.9142 to g.9232 within GeneBank Accession No. KU501215) is detected for the Zika virus NS5 mRNA.

It should be noted that both the 73-bp amplicon and the 91-bp amplicon can be used separately or in conjunction for confirmatory testing. In some embodiments, it has been surprisingly found that the 91-bp amplicon shows increased sensitivity, with a Limit of Detection (LOD) of 400 viruses detected in 1 mL of semen sample. The 73-bp assay gave an LOD of 2000 viruses detected per mL of semen sample. All the critical data was generated from Live Zika Virus, using the PRVABC59 strain isolated in Puerto Rico in 2016.

Sequence alignment confirms the sequence conservation between the primer and probe sets for both the 73-bp and 91-bp amplicons disclosed herein compared to Zika isolates representing Zika virus circulating in the Americas. The Zika sequences from Metsky et al. (Zika virus evolution and spread in the Americas. Nature. 2017; 546: 411-415) were retrieved from Genbank and are considered preliminary sequence data since they were generated from ‘first run’ sequence runs from new viral isolates and may not be considered fully validated data. However, when comparing the primer and probe alignments of the 73-bp and 91-bp amplicons, very good conservation is observed indicating assays built on these primer/probe sets would successful detect all of the Zika isolates circulating at the time of the study. Most importantly, the sequences corresponding to the probe regions are highly conserved and secondly, so are those of both the reverse primers. In Reverse Transcription Polymerase Chain Reaction (RT-PCR), the reverse primer is essential for generating the cDNA from the viral RNA template, which is the first critical step for successful RT-PCR. With successful cDNA copies of the viral RNA target, subsequent PCR amplification can proceed with maximum efficiency, followed by detection by hydrolysis of the matched probes as presented herein. In cases where a single-mismatch does occur, such as in the forward primer sequences, no mismatches at the 3' end of primer have been found. As for probe sequences, the probes disclosed herein can be generated from either the positive or minus strand of the template or be extended or shortened by a few bases to adjust to changing variation in the Zika genome as future sequence data is added to the existing data base.

DNA-Based PCR for Virus Associated with Human Semen

Sperm banks follow standard FDA guidelines to qualify their donors prior to releasing semen for reproduction. These qualifications include medical history, sexual activity history, physical exam and blood-based tests to detect the presence of viruses and bacteria and/or the presence of antibodies in the bloodstream directed against these pathogens. However, the direct testing of semen is not necessary as part of the FDA regulations. This position is shortsighted, since there is evidence that semen obtained from qualified donors can contain virus and bacteria that slip through the cracks of standard screening protocols. Viruses such as cytomegalovirus (CMV), human papillomavirus types 16 & 18 (HPV 16 & 18), herpes simplex virus types 1 & 2 (HSV 1 & 2), and now Zika (ZIKV) virus can remain in the testes in latent form in the absence of symptoms and potentially can be passed to recipients of donor semen. All these viruses can have harmful effects on developing fetuses, and in the case of high risk HPV strains 16 & 18, can result in cervical cancer in women who contract these viruses from infected semen.

Disclosed herein are molecular diagnostic assays for semen testing for these clinically important viruses. The semen test is comprised of a multiplex panel including primers and probes for Zika, CMA, HPV 16 & 18, HSV 1 & 2 and internal positive controls detecting a donor-derived gene sequence (DNA control) and a ubiquitously expressed mRNA (RNA control). For each semen sample, an RNA-based RT-PCR reaction is used for Zika detection and a DNA-based PCR reaction is used for CMV, HPV, and HSV detection, including their respective internal positive controls.

The following examples are set forth as being representative of the present disclosure. These examples are not to be construed as limiting the scope of the disclosure as these and other equivalent embodiments will be apparent in view of the present disclosure and accompanying claims.

EXAMPLES

Example 1

Materials and Methods for Zika Virus Detection

Reagent Preparation—All stock regents are handled according to manufacturer's instructions with respect to storage, temperature, and expirations dates:
Qiagen QIAamp® Viral RNA Mini kit (Qiagen catalog #52904 or 52906)
Qiagen QIAmp® RNeasy RNA Mini kit (Qiagen catalog #61904)
SuperScript® III Platinum® One-Step qRT-PCR Kit (ThermoFisher catalog #11732088 or 11732020)
Cepheid Smartcycler® II, Cepheid Inc. (catalog # SC2500 N 1-1 or SC2500 N 1-2)
SuperScript® III Platinum® One-Step qRT-PCR Kit contains SuperScript™ reverse transcriptase and Platinum™ Taq polymerase, and includes 2x reaction buffer containing $Mg^{++}$ yielding a final concentration of 3.2 uM.
Primers/Probe set—Forward and Reverse primers and hydrolysis probes are maintained as 100 uM stock aliquots. Forward and Reverse primer stocks are mixed using equal volumes yielding a mixture of 50 uM for each primer. This mixture is diluted to final volume during assay set-up using a preset Excel macro containing the proper dilution calculations based on the number of reactions and final assay volume.

Zika Virus (ZIKV) First primer/probe set-NS5 gene (73-bp amplicon):

```
Forward:
                                     (SEQ ID NO: 1)
5'-CAA AAC AAA GTG GTA AAG GT-3'

Reverse:
                                     (SEQ ID NO: 2)
5'-CTT GTC TCG AAA TAA TGT CC-3'

Probe:
                                     (SEQ ID NO: 3)
5'-Reporter-CTT AGA CCA GCT GAA AAA GGG AA-
Quencher-3' BHQ
```

Zika Virus (ZIKV) Second (alternative) primer/probe set-NS5 gene (91-bp amplicon):

```
Forward:
                                     (SEQ ID NO: 4)
5'-CTT GAA CGA GGA TCA CT-3'

Reverse:
                                     (SEQ ID NO: 5)
5'-CTC TTC TAG GAC ATA TCC GA-3'

Probe:
                                     (SEQ ID NO: 6)
5'-Reporter-TCC CAG CCC TTC AAC ACC-
Quencher-3' BHQ
```

Internal Positive RNA control (donor/patient derived) mRNA sequence (ubiquitously expressed beta Actin gene, ACTB):

```
Forward:
                                     (SEQ ID NO: 7)
5'-CGC GCT CGT CGT CGA CA-3'

Reverse:
                                     (SEQ ID NO: 8)
5'-CCA CCA TCA CGC CCT GGT-3'

Probe:
                                     (SEQ ID NO: 9)
5'-Reporter-ACG GCT CCG GCA TGT GCA A-Quencher-3'
```

RT-PCR reaction setup: A single reaction is performed in a 25-uL volume. Each reaction is composed of the following components:
12.5 uL of 2×RT-PCR buffer (Qiagen)
0.2 uL of Forward Zika primer at [50 uM] (final conc. 0.4 uM, range 0.2 to 0.8 uM)
0.2 uL of Reverse Zika primer at [50 uM] (final conc. 0.4 uM, range 0.2 to 0.8 uM)
0.2 uL of Zika hydrolysis probe at [50 uM] (final conc. 0.4 uM, range 0.2 to 0.8 uM)
0.25 uL of Forward ACTB primer at [10 uM] (final conc. 0.1 uM, range 0.08 to 0.4 uM)
0.25 uL of Reverse ACTB primer at [10 uM] (final conc. 0.1 uM, range 0.08 to 0.4 uM)
0.5 uL of ACTB hydrolysis probe at [10 uM] (final conc. 0.2 uM, range 0.1 to 0.4 uM)
0.1 uL of SS Enzyme mix at [1 U/uL] (final conc. 0.04 U/uL, range 0.01 to 0.08 U/uL)

5.8 uL sterile, water
5.0 uL template (extracted RNA from clinical specimen)
25.0 uL total volume
Real-time RT-PCR thermocycling profile:
Step 1) Reverse Transcription Reaction—
50° C., 45 minutes×1 cycle
Step 2) Polymerase Chain Reaction—
Stage 1: 45 min at 50° C.; 1×
Stage 2: 2 min at 95° C.; 1×
Stage 3: 15 sec at 95° C.
Stage 4: 15 sec at 50° C.
Stage 5: 15 sec at 72° C.
Repeat stages 3-5, 49× (50 cycles total)
Step 3): hold at 4° C.

Real-time RT-PCR is a closed tube method. Tubes can be discarded after use to avoid cross-contamination of end-product.

Assay controls including a patient-derived internal positive and appropriate negative controls are run concurrently with all test samples.

Extraction Control: Excess human semen obtained with patient consent by an FDA registered cryobank was used for specimen extractions and test development. Semen samples were previously tested for the presence of HSV 1 & 2, CMV and high risk HPV by PCR and only negative semen samples were used herein. For RNA-based infectious targets, all clinical assays include the detection of a patient derived ubiquitous mRNA for the beta-actin gene (ACTB) to serve as an internal positive control to monitor RNA extraction, cDNA synthesis, amplification and detection in the same tube as the specimen. This allows the identification of false negative results due to assay failure at any of the key points mentioned above. The primers for the ACTB mRNA are placed in adjacent exons separated by a large intervening sequence (>1-kb) such that genomic DNA does not yield a signal in rapid cycle rRT-PCR. In mature mRNA however, the co-joined exons yield a 101-bp product detected only when intact RNA is present indicating successful RNA extraction, cDNA synthesis, amplification and fluorescence detection. This human primer/probe set does not cross react with any of the pathogen sequences tested in the clinical testing program, or with Zika and related flaviviruses.

Positive Controls for Zika-specific Detection using Primer/Probe Set:

Zika virus strain MR776—live virus stock and extracted viral RNA

Zika virus strain KU501215 (PVR ABC59)—live virus stock and extracted RNA

Zika virus single-stranded synthetic RNA template, 118 nucleotides

It should be noted that synthetic RNA template is an ideal positive control measurand for several reasons. It was synthesized under strict GMP guidelines by a qualified commercial vendor (BioSciences, Inc.) and purified by reverse-phase HPLC and analyzed by high resolution PAGE. The concentration was determined by the vendor; 0.516 OD× (0.79 nmole/$OD_{260}$)=0.408 nmole, and 0.516 OD×(31.01 ug/$OD_{260}$)=16 ug total. This information provides precise determination of genome equivalents per mL of sample (number of full length molecules per mL). The 73-bp amplicon is centrally located in the 118-base sequence with 22 and 24 nucleotides flanking the amplicon, upstream and downstream, respectively. The entire 118-base sequence is identical to genomic positions g.9366 to g.9484 of NS5 from strain KU501215 (Zika PRV ABC59). In silico analysis of this sequence shows 100% homology to all Brazil isolates listed on GenBank (from the Americas), including KU501215, with one mismatch to French Polynesia strain KJ776791 and Yap Island strain EU45988 at a position not included in the GIFV-ZIKV primer/probe set. In addition, this template is non-infectious providing an extra measure of safety during large scale studies using contrived positives covering a wide range of highly accurate input titers.

Viral positive controls are used for serial dilutions (dynamic range) and limit of detection studies and are included in all Zika assay runs. Extracted viral nucleic acids are aliquoted and stored at −80° C. until use and only used once post-thaw.

Negative (no) Template Control (NTC): NTC reactions are included for every rRT-PCR run. Molecular-grade water (DNase/RNase-free) is used in place of specimen nucleic acid and must be included for each reaction mixture in each run. The NTC is a control for contamination or improper function of assay reagents resulting in false positive results.

Acceptable Specimens: Semen collected under sterile conditions according to standard instructions in a sterile vial (for example, urine collection bottle) is stored at 4° C., or frozen at −20° C. prior to shipping or testing.

Specimen Handling and Storage: Human specimens are transported in accordance with all applicable regulations for transportation of potentially infectious biological specimens. Human semen specimens are shipped on dry ice, when possible. Cold packs (frozen) can be used for overnight, next-day delivery using specified Styrofoam shipping containers. Specimens are stored at −20° C. upon receipt in lab. Thawed specimens are processed immediately and kept cold (4-8° C.) during sample processing. Excess sample is stored at −70° C. for long term storage.

Nucleic Acid Extraction: Sample nucleic acid extractions have been validated for use on whole semen, washed semen (1×PBS) and cryopreserved semen processed for storage and semen donation. Data for whole and washed semen extraction is detailed below. If washed semen was used for any validation steps, those data will be noted. Two Qiagen, column-based, RNA mini kits have been tested for this study. Briefly, the Viral RNA mini kit yields intact RNA and full length DNA. The Qiagen RNeasy mini kit yields primarily intact RNA by a column separation step that excludes bulk DNA from the final eluate. Semen contains fairly high cellular content, thus eliminating bulk DNA may aid in the detection of RNA targets.

Manual Extraction Protocol: All extraction steps are performed in accordance with manufacturer's instructions. Extractions are performed in a sterile BLS-2 biocontainment hood. Prepare a specimen extraction run log using template as directed in SOP and fill in required specimen list, accession numbers, date, number of samples and technician initials. Calculate the number of Qiagen extractions tubes and columns needed for each run. Label extraction tubes accordingly with permanent ink according to the extraction run log. Prepare all extraction buffers and solutions according to protocol instructions.

Specimen input volume: 200 uL whole (raw) semen. For washed samples, 200 uL of whole semen are added to 400-500 ul of sterile 1×PBS, mixed gently, centrifuged at 5,000 g for 5 minutes, and the cellular pellet is recovered in 200 uL of residual supernatant and used for subsequent extraction. Typically, 200 uL of semen contains $2$-$4 \times 10^6$ sperm cells, $1$-$5 \times 10^4$ white blood cells, various amounts of fructose, citrate, zinc, proteins, carbohydrates, mucus, etc. Washed semen contains all the cellular components including white cells after pelleting, minus many of the cell-free components. Washed cell pellets are resuspended in residual PBS buffer from the wash step. When feasible, whole (raw)

semen is used as specimen, increasing the probability of detecting virus, the titer of which may be reduced by the wash step. However, any infected cells (WBC from seminal fluid) bearing replicating virus will be included in the cell pellet after washing, as well as cell-free virus remaining in the 200-uL wash buffer used for pellet resuspension.

Extracted nucleic acid is eluted with 60 uL of provided AE Buffer. After the first elution, the same eluate is added back to the column and a second column recovery is performed to collect any nucleic acid not release the first time. The final elution volume is 52-55 uL. Specimen extracted nucleic acid is used immediately for rRT-PCR testing.

Storage of Nucleic Acid Specimens: Specimen RNA extracts are kept on ice (or 4° C. cold block) until testing assay setup is complete. Excess specimen extract is stored at −80° C. Once frozen, extracted RNA should not be subjected to more than one or two freeze/thaw cycles for subsequent testing, if necessary.

rRT-PCR Assay Setup: Prepare a SmartCycler protocol sheet for GIVF-ZR RT-PCR (see below) including samples and controls (see Table 1).

TABLE 1

SAMPLES.

| Tube # | Sample ID | Notes |
| --- | --- | --- |
| 1 | Acc. # 49308 - Semen | Test sample |
| 2 | Acc. # 49308 | Test sample |
| 3 | Acc. # 49309 - Semen | Test sample |
| 4 | Acc. # 49309 | Test sample |
| 5 | Acc. # 49310 - Semen | Test sample |
| 6 | Acc. # 49310 | Test sample |
| 7 | Acc. # 49471 - Semen | Test sample |
| 8 | Acc. # 49471 | Test sample |
| 9 | Acc. # 49472 - Semen | Test sample |
| 10 | Acc. # 49472 | Test sample |
| 17 | Zika Synthetic RNA 1 ($10^{-7}$) | Positive control |
| 18 | Zika Synthetic RNA 2 ($10^{-7}$) | Positive control |
| 18 | Human RNA Control | Human Beta-actin target |
| 19 | Negative control - H20 | Negative control |

Positive Controls:

1) Zika. Viral RNA used for Zika detection (KU501215 or synthetic RNA template) must be positive and within the expected Ct value range. If Zika assay controls are negative, or entire run must be repeated after corrective action is taken. If Zika positive controls continue to fail, new positive control template must be tested and confirmed before using in subsequent runs.

2) Extraction control using ACTB mRNA. Detection of the patient derived, ubiquitous ACTB (beta-actin) mRNA must be present in all patient samples and within the expected Ct range for semen testing. If this internal positive control is absent, either extraction of intact RNA failed, inhibitors were present in sample, reagents or primer/probe sets failed or the RT or Taq enzyme failed. If the control sample containing purified human RNA (from a negative blood sample) tested in parallel also failed, that suggests an enzyme or Master Mix reagent failure. If this control is positive for ACTB mRNA in the control lane (as expected), then the failed semen samples may contain degraded RNA or an enzyme inhibitor and must be re-extracted and re-tested. If an inhibitor is suspected, then a 'clean-up' step as outlined in Lab SOP must be followed prior to retesting.

Negative Controls: The water only reactions must be negative for Zika products and for human mRNA for ACTB. The human RNA from negative blood should also be negative for Zika RNA but positive for ACTB mRNA (see above). If any negative controls are inappropriately positive, follow procedures outlined in lab SOP; clean potential nucleic acid contamination from bench surfaces and pipettes in the reagent setup and template addition work areas, test new water sources, extract and test new negative blood draws, discard working reagent solutions and remake from fresh stocks, and repeat samples that may have been tainted by contamination or in any way compromised.

TABLE 2

Positive ("pos") and negative ("neg") control performance:

| Type (Pos/Neg) | Name | Use | Zika | Human RNA | Ct values |
| --- | --- | --- | --- | --- | --- |
| Positive | Zika RNA | Monitor reagent master mix, enzyme, primer/probe failure | (+) | (−) | 30-40 Ct |
| Negative | No template control (water) | Contamination at any step in assay | (−) | (−) | N/D |
| Nucleic Acid Extraction* | Patient derived internal positive control | Monitor nucleic acid integrity, enzyme inhibition, reagent or enzyme failure, contamination | (−) (+) in positive samples | (+) in all patient samples & human RNA control | 28-40 Ct |

*Note:
All clinical RNA-based assays include the detection of a patient derived ubiquitous mRNA for the beta-actin gene (ACTB) to serve as an internal positive control to monitor extraction, cDNA synthesis, amplification and detection in the same tube as the specimen, allowing the identification of false negative results due to failure of the assay at any point.

Example 2

Results for Zika Virus Detection Using the 73-Bp Amplicon

In this example, results for Zika virus detection using the 73-bp amplicon are shown. Briefly, using the materials and methods in Example 1, the 73-bp amplicon is targeted using SEQ ID NOs: 1-3.

GIVF-ZIKV positive and negative controls: Table 3 describes the utility of positive and negative control reactions required to monitor GIVF-ZIKV assay performance. The data must be examined and considered valid before any interpretation of patient results can be made.

TABLE 3

GIVF-ZIKV positive ("pos") and negative ("neg") controls

| Type (Pos/Neg) | Name | Use | Zika | Human RNA | Ct values |
|---|---|---|---|---|---|
| Positive | Zika RNA | Monitor reagent master mix, enzymes, primer/probe failure | (+) | (−) | 28-40 Ct |
| Negative | No template control (water) | Contamination at any step in assay | (−) | (−) | N/D |
| Nucleic Acid Extraction | Patient derived internal positive control | Monitor nucleic acid integrity, enzyme inhibition, reagent or enzyme failure, contamination | (−) (+) in positive samples | (+) in all patient samples & human RNA control | 28-40 Ct |

Zika Positive Control. As described above, only reactions containing Zika template should be positive (Zika positive control), unless a patient sample is positive (in duplicate). In that case, examine the human RNA control and NTC control; if these controls are negative for Zika, then the Zika-positive results for the patient are valid, as long as all other controls are as expected (see below). If the human RNA control or the NTC are positive for Zika, the entire run is invalid due to contamination of reagents or sample cross-contamination from a strongly positive sample or samples. If Zika positive control is negative, the assay is invalid and all reactions are repeated with new positive control template and primer/probe mix.

No Template Control Negative Control (water). The NTC must be negative for all assay targets. If amplification product is detected in NTC, determine if it is FAM or TET to narrow the source of contamination. FAM indicates contamination with viral template, most likely from positive control material. TET indicates contamination from human RNA showing product for human ACTB mRNA. In any case of contamination, the entire assay must be repeated using procedures outlined in lab SOP: remove potential nucleic acid contamination from bench surfaces and pipettes in the reagent setup and template addition work areas, test new water sources, discard working reagent solutions and remake from fresh stocks, and repeat samples that may have been tainted by contamination or in any way was compromised.

Extraction Positive Control Using ACTB mRNA. Detection of the patient derived, ubiquitous ACTB (beta-actin) mRNA must be present in all patient samples and within the expected Ct range for semen testing. If this internal positive control is absent, either extraction of intact RNA failed, inhibitors were present in sample, or the RT or Taq enzyme failed. If the control sample containing purified human RNA (from a negative blood sample) tested in parallel also failed, that suggests an enzyme or Master Mix reagent failure. If this control is positive for ACTB mRNA in the control lane (as expected), then the failed semen samples may contain degraded RNA or an enzyme inhibitor and must be re-extracted and re-tested. If an inhibitor is suspected, then a 'clean-up' step as outlined in the SOP must be followed prior to retesting.

For each GIVF-ZIKV assay, the data for positive and negative controls must conform to Table 3 above. Any deviation from these results must be evaluated using the criteria described above and corrective action taken in light of the aberrant results and repeat testing performed as appropriate.

After examination of positive and negative controls verifies the validity of the assay to this point, assessment of clinical specimen test results can proceed. The GIVF-ZIKV qualitative assay must be positive in duplicate for a given patient sample with Ct values in the range from 25-28 (strong), 29-32 (moderate), and 33-40 (weak) and report as DETECTED. Any patient results that are negative, in duplicate, are reported as NOT DETECTED. Discordant patient results (one of two positive) must be repeated until an unequivocal result is achieved, regardless of Ct value. Any patient results showing Ct values above 40 Ct, or weak growth curves without definitive exponential log phase, linear phase and plateau phase profiles must be considered negative and repeated until a profile indicative of a true positive is observed. If retesting shows the same weak growth curves, the sample is reported as negative. It must be noted that in the case of strong Zika positive growth curves representing abundant amplification product for the virus, the patient derived internal positive control for ACTB mRNA may be suppressed. The relative strength of the two possible products (Zika versus ACTB mRNA) is such that the viral target is a more robust reaction and the ACTB mRNA may not reach threshold. This is an assay design feature and prevents a weak viral positive from being obscured by the internal control reaction occurring simultaneously in the single-tube format.

The analytical sensitivity of the GIVF-ZIKV Assay was determined by performing multiple serial dilution experiments to determine the Limit of Detection ("LoD"): the lowest detectable concentration of Zika virus at which approximately 95% of all replicates (true positive) test positive. The limiting dilution studies were performed using human semen containing known viral dilution points that was subjected to nucleic acid extraction, rRT-PCR and fluorescence detection using the protocol as described in detail in previous sections of the application.

The Zika sequences included in the GIVF-ZIKV primers/probe set are 100% conserved in all Zika strains isolated in the Americas posted on GenBank. Zika strain PRV ABC59

(KU501215, Puerto Rico, March, 2016) was used for wetwork testing and used in all serial dilution and LoD studies. The original titer of the viral stock was $1\times10^{6.34}$ TCID$_{50}$ units per mL or $1.5\times10^6$ PFU per mL, as provided by the commercial vendor, Zeptometrix, Inc.

Multiple serial dilution experiments were performed using either live viral stock, extracted viral RNA or synthetic RNA containing a 118-nucleotide sequence (from KU501215) encompassing the amplicon. The use of live virus in dilution studies was initially necessary to verify that the extraction methods tested were capable of capsid disruption, lysis and recovery of intact viral RNA in a background of 200-uL of human semen. However, TCID$_{50}$ and PFU values cannot be easily converted to the exact genome copy number (genome copy equivalents) since this is an error-prone virus with a percentage of defective (non-viable) particles. Therefore, to determine LoD with respect to genome copy equivalents ("GCE"), extracted viral RNA from the live viral stock, or synthetic RNA template was used for serial dilutions. For extracted viral RNA, precise OD$_{260}$ absorbance data was used to calculate genome copy number for a 10-kilobase, single-stranded viral RNA genome. When using the synthetic RNA template, data provided by the vendor (see previous sections) and confirmed by NanoDrop absorbance data provided an exact RNA titer with respect to GCE/mL (template molecules/mL).

Whether using quantified extracted viral RNA or synthetic RNA template for semen serial dilution and LoD studies, both approaches produced very similar rRT-PCR data and Ct values at each dilution point. To ensure precision, accuracy and reproducibility throughout the entire validation process, the synthetic RNA template derived from strain KU501215 sequence is a superior analyte since the exact number of full length molecules (or moles) per mL is known and the construct was designed to include an inverted deoxynucleotide (dT) at the 3' end to prevent degradation during storage and handling.

TABLE 4

Study comparing two Qiagen nucleic acid extraction methods.

| # | Sample & dilution factor* | FAM+ Ct | TET++ Ct |
|---|---|---|---|
| 1 | Semen, Viral RNA kit + ZKV (−7) | 28.19 | 26.86 |
| 2 | Semen, Viral RNA kit + ZKV (−7) | 29.24 | 27.67 |
| 3 | Semen, RNeasy kit + ZKV (−7) | 28.38 | 34.54 |
| 4 | Semen, RNeasy kit + ZKV (−7) | 27.35 | 32.31 |
| 5 | ZKV (+) control (−5) | 20.13 | 0 |
| 6 | Blood RNA | 0 | 43.99 |
| 7 | Semen RNA, no ZKV | 0 | 28.90 |
| 8 | Semen RNA, no ZKV | 0 | 28.09 |
| 9 | NTC (water) | 0 | 0 |

*Zika synthetic RNA template was added to 200-uL of whole semen, in duplicate, and extracted using the Qiagen Viral RNA or RNeasy method and tested by assay GIVF-ZIKV at a of $1 \times 10^{-7}$ dilution ($2 \times 10^5$ GCE/ml).
+FAM, detection of Zika amplicon
++TET, detection of internal positive control; ACTB (beta-actin) mRNA (patient derived)

Limit of Detection: Multiple serial dilution studies were performed using a 10-fold dilution factor and initially extended over 10 orders of magnitude using full strength analyte as starting point. An example of a dilution series from $1\times10^{-4}$ to $1\times10^{-11}$ is shown in Table 5 using nucleic acid isolated from Zika negative washed semen as a test matrix.

TABLE 5

| # | Sample & dilution factor* | FAM Ct |
|---|---|---|
| 1 | Human semen, ZV at −4 | 15.67 |
| 2 | Human semen, ZV at −4 | 14.40 |
| 3 | Human semen, ZV at −5 | 18.32 |
| 4 | Human semen, ZV at −5 | 18.41 |
| 5 | Human semen, ZV at −6 | 22.09 |
| 6 | Human semen, ZV at −6 | 22.19 |
| 7 | Human semen, ZV at −7 | 25.93 |
| 8 | Human semen, ZV at −7 | 26.22 |
| 9 | Human semen, ZV at −8 | 29.50 |
| 10 | Human semen, ZV at −8 | 29.71 |
| 11 | Human semen, ZV at −9** | 32.65 |
| 12 | Human semen, ZV at −9** | 32.26 |
| 13 | Human semen, ZV at −10 | 0 |
| 14 | Human semen, ZV at −10 | 0 |
| 15 | Human semen, ZV at −11 | 0 |
| 16 | Human semen, ZV at −11 | 0 |
| 17 | Human semen, ZV no Zika | 0 |
| 18 | Human semen, ZV no Zika | 0 |

*Zika synthetic RNA template was added to 200-uL of washed semen (1xPBS, as described), in duplicate, and extracted using the Qiagen Viral RNA method and tested by assay GIVF-ZIKV. The dilution factor (−4 to −11, 10-fold dilution series) is shown. Synthetic Zika RNA template was used due to precision of calculating genomes per mL.

Table 6 is an example of a serial dilution series using whole, unwashed human semen as matrix. The Zika RNA template was added to 200-uL of human semen and extracted as described above.

TABLE 6

| # | Sample & dilution factor* | FAM Ct |
|---|---|---|
| 1 | Human semen, ZV at −6 | 22.31 |
| 2 | Human semen, ZV at −6 | 22.11 |
| 3 | Human semen, ZV at −7 | 26.76 |
| 4 | Human semen, ZV at −7 | 27.20 |
| 5 | Human semen, ZV at −8 | 31.66 |
| 6 | Human semen, ZV at −8 | 31.78 |
| 7 | Human semen, ZV at −9** | 35.74 |
| 8 | Human semen, ZV at −9** | 36.57 |
| 9 | Human semen, ZV at −10 | 0 |
| 10 | Human semen, ZV at −10 | 0 |
| 11 | Human semen, ZV at −11 | 0 |
| 12 | Human semen, ZV at −11 | 0 |
| 13 | Human semen, ZV no Zika | 0 |
| 14 | Human semen, ZV no Zika | 0 |

*Zika synthetic RNA template was added to 200-uL of whole (raw) semen, in duplicate, and processed as above.

As expected, using whole (raw) semen yielded higher Ct values (lower sensitivity) compared to washed sample, particularly at lower viral RNA inputs, due to the complexity of the specimen type. However, testing whole semen will increase the probability of virus detection since no virus would be potentially lost during the wash step.

Once an LoD is achieved, the dilution factor can be converted to genome copy equivalents ("GCE") per mL of semen. In these experiments the original GCE of the stock (undiluted) can be used to convert the dilution factor to a GCE/mL value. Data shown below incorporates GCE/mL values for the dilution factors used above. For example, the starting concentration of Zika viral RNA template was $8\times10^{13}$ genomes per mL ($8\times10^{10}$ per uL) based on in-house NanoDrop absorbance$_{260}$ values consistent with information provided by the vendor. For each dilution point, 5-uL of viral RNA is added to 200-uL of semen sample. For the LoD estimated from the data above, 400 [5× ($8\times10^1$)] genomes were added to 200 uL semen, or 2000 genomes per mL. The 200-uL semen sample is extracted (as described previously), and eluted in 50-uL of elution buffer, followed by the addition of 5-uL into each rRT-PCR assay. Therefore, 400

GCE were collected in 50-uL (8 GCE/uL) and 5-uL (40 GCE) was added to rRT-PCR, yielding a detection of 40 GCE per reaction, or 2000 GCE/mL, consistent with the other GIVF rRT-PCR and PCR assays in use in the lab. (Typically, a detection threshold of 5-20 template copies per 5-uL assay is achieved for DNA PCR and 10-50 copies for RNA RT-PCR, depending on pathogen.) The data from Table 6 above is shown in Table 7 with respect to GCE/mL.

TABLE 7

| # | Sample & dilution factor | GCE/mL | FAM Ct |
|---|---|---|---|
| 1 | Human semen, ZV at −6 | $2 \times 10^6$ | 22.31 |
| 2 | Human semen, ZV at −6 | $2 \times 10^6$ | 22.11 |
| 3 | Human semen, ZV at −7 | $2 \times 10^5$ | 26.76 |
| 4 | Human semen, ZV at −7 | $2 \times 10^5$ | 27.20 |
| 5 | Human semen, ZV at −8 | $2 \times 10^4$ | 31.66 |
| 6 | Human semen, ZV at −8 | $2 \times 10^4$ | 31.78 |
| 7 | Human semen, ZV at −9* | $2 \times 10^3$ | 35.74 |
| 8 | Human semen, ZV at −9* | $2 \times 10^3$ | 36.57 |
| 9 | Human semen, ZV at −10 | $2 \times 10^2$ | 0 |
| 10 | Human semen, ZV at −10 | $2 \times 10^2$ | 0 |
| 11 | Human semen, ZV at −11 | $2 \times 10^1$ | 0 |
| 12 | Human semen, ZV at −11 | $2 \times 10^1$ | 0 |
| 13 | Human semen, ZV no Zika | 0 | 0 |
| 14 | Human semen, ZV no Zika | 0 | 0 |

*LoD equals $2 \times 10^3$ GCE/ml whole unwashed semen. Any Ct equal to or above Ct 40 is considered negative. LoD for this run corresponds to a $1 \times 10^{-9}$ factor of stock.

SUMMARY

Serial dilutions of the characterized Zika virus were tested in nine experiments (at least three studies were performed using as template live virus, extracted viral RNA and synthetic Zika RNA added to human washed and whole semen). Consistent with Lab clinical testing program in which each patient specimen is run in duplicate, serial dilution studies were designed such that each dilution point was run six times: in duplicate in three independent runs. The lowest concentration at which all replicate reactions were positive was treated as the tentative LoD for Zika ($2 \times 10^3$ GCE/mL, Ct ~36 for whole semen). The LoD of each test was then confirmed by testing 20 replicates with concentrations at the tentative limit of detection. The final LoD of each test was determined to be the lowest concentration resulting in positive detection of 20 out of 20 replicates as shown below in Table 8.

TABLE 8

| # | GCE/mL | Zika positive (#) | Average Ct |
|---|---|---|---|
| 1 | $2 \times 10^6$ | 20/20 | 22.24 |
| 2 | $2 \times 10^5$ | 20/20 | 26.82 |
| 3 | $2 \times 10^4$ | 20/20 | 31.63 |
| 4 | $2 \times 10^3$ | 20/20 | 36.47 |
| 5 | $2 \times 10^2$ | 0/20 | 0 |

Reactivity/Inclusivity: For in silico inclusivity evaluation, a BLAST (NCBI) analysis was performed using the 73-nucleotide NS5 gene sequence of Zika strain KU501215 (Zika PRV ABC529) isolated February, 2016 and posted on GenBank March, 2016. The GIVF-ZIKV amplicon showed 100% sequence identity with over 100 entries including all isolates from the South and Central America and the Caribbean. When compared to Asian (Malaysian) and Polynesian strains, i.e. French Polynesia strain KJ776791 and Yap Island strain EU45988, one mismatch is found but not within the GIVF-ZIKV primers/probe region. An additional mismatch was found with Yap Island strain EU45988 near the 5'-end of the reverse primer. The NS5 gene was chosen as the target due to its high conservation in American Zika strains and its degree of mismatch with other flaviviruses based on in silico and wet-work analysis. Due to the unavailability of obtaining many of the new world strains and the lack of commercial positive control material based on the relevant new isolate sequences, wet-work with PRV ABC529 and the derived synthetic RNA template was the most feasible approach for an emergency use application to prevent sexual transmission of this teratogenic pathogen.

Cross Reactivity: Cross-reactivity of the GIVF-ZIKV was evaluated by testing additional flaviviruses or purified nucleic acid from other microorganisms. In silico analysis comparing the GIVF-ZIKV primer/probe set to related flaviviruses showed minimal homology to Chikungunya virus, to the extent that no possible cross-reactivity is possible. Of the Dengue strains (1-4), only Dengue-4 ($TCID_{50}$ $1 \times 10^{6.18}$ U/ml) showed any possible cross-reactivity and was wet-tested below, along with Yellow Fever ($TCID_{50}$ $1 \times 10^{6.02}$ U/ml) and West Nile ($TCID_{50}$ $1 \times 10^3$ copies/ml) viruses.

TABLE 9

Cross Reactivity: Wet-testing with RNA extracted from stock of known titer (above).

| Virus | Strain | Source/Sample type | Concentration | Ct Value |
|---|---|---|---|---|
| Yellow Fever Virus | 17D | RNA extracted from live virus | $2 \times 10^7$ GCE/mL | 0 |
| Yellow Fever Virus | 17D | RNA extracted from live virus | $2 \times 10^6$ GCE/mL | 0 |
| Dengue Virus type-4 | H241 | RNA extracted from live virus | $2 \times 10^7$ GCE/mL | 0 |
| Dengue Virus type-4 | H241 | RNA extracted from live virus | $2 \times 10^6$ GCE/mL | 0 |
| West Nile Virus | NY 2001-62263 | RNA extracted from live virus | $2 \times 10^7$ GCE/mL | 0 |
| West Nile Virus | NY 2001-62263 | RNA extracted from live virus | $2 \times 10^6$ GCE/mL | 0 |

Additional wet-testing involved performing GIVF-ZIKV with positive control nucleic acid from the other pathogens tested as part of the Lab's clinical testing program. This was incorporated into the regular quality control, quality assurance schedule where by all analytes are tested for reactivity. The GIVF-ZIKV Assay was run against the following positive control material using the 'high' positive titer for each target. No cross-reactivity was detected. Particular attention was directed at those pathogens known to be transmitted sexually, and that are included in the Lab's semen testing program designed to exclude semen positive for HSV 1 & 2, CMV, or high-risk HPV from donation.

Pathogens wet-tested: Herpes Simplex Virus 1 & 2, VZV, CMV, EBV, Human Herpesvirus-6, HIV-1, HIV-2, HTLV I/II, enterovirus, Parvovirus B-19, Toxoplasma gondii, HPV 16 & 18, Chlamydia trachomatis, Neisseria gonorrhoeae, Mycoplasma genitalium, Ureaplasma urealyticum. No cross-reactivity was detected using (high) titers ranging from $1 \times 10^5$ to $1 \times 10^7$ GCE/mL.

Additional in silico analysis using BLAST (NCBI) performed against the following microorganisms demonstrated no sequence conservation supporting primer/probe cross-reactivity. As stated above, the closest identify between GIVF-ZIKV and other flaviviruses was with Dengue-4. The other organisms tested are listed below: Bacteria (taxid 36470/590/64895/1239), Fungus (5036), Eastern Equine Encephalitis Virus (11021), Western Equine Encephalitis Virus (11039), Ross River Virus (11029), Barmah Forest Virus (11020), Chikungunya Virus (37124), Mayaro Virus (59301), Hepatitis C Virus (11103), Enterovirus (all serotypes, 12059), Adenovirus (all serotypes, 108098, 130310, 129951, 565302,10519), Hepatitis B Virus, HIV (11676), Trypanosoma cruzi (5693), Borrelia burgdorferi (64895), Rickettsia (780), Influenza A (11320), Influenza B (11520), Vaccinia (10245), Rubella (11041), Measles Virus (11234).

The existing semen testing program is utilized to exclude from donation semen that contains the presence of HSV 1 & 2, CMV, and HPV strains 16 & 18, as well as Chlamydia trachomatis and Neisseria gonorrhoeae when requested by a physician. Since these are DNA agents and a DNA-specific extraction method was previously used, we have migrated to a Qiagen method yielding intact RNA and DNA in order to eventually include a Zika testing option when appropriate. A prospective clinical study is underway using GIVF-ZIKV to generate data for emergency use, if authorized, for Zika detection.

To date, 48 whole (raw) semen specimens collected in Brazil from a Sao Paulo cryobank have been tested using GIVF-ZIKV. All samples tested negative. Additionally, a US cryobank has supplied 30 whole semen samples collected from five individuals excluded from semen donation who had a history of travel to Zika-circulating countries (Mexico, Brazil, Puerto Rico and Dominion Republic). These specimens also tested negative using the GIVF-ZIKV Assay. In total, data from 78 negative specimens has been generated. As part of the Lab's ongoing semen testing program in association with the Fairfax Cryobank, 12-15 new specimens received weekly are undergoing RNA and DNA extraction. Excess semen remaining after HSV 1 & 2, CMV, and HPV testing is available for GIVF-ZIKV validation. The data from semen samples testing negative for Zika using GIVF-ZIKV can be added to the prospective study data set. To date, over 400 donor semen samples have been tested for Zika. In addition, this excess Zika-negative semen has been used for generating contrived positive samples of known viral titers and subjected the GIVF-ZIKV assay as described, including nucleic acid extraction, rRT-PCR and data analysis.

The serial dilution and limit of detection studies performed to date have demonstrated an LoD of $2\times10^3$ GCE/mL using 200-uL whole (unwashed) semen extracted using Qiagen Viral RNA mini kit and tested using the GIVF-ZIKV rRT-PCR assay. Based on only a few publications that quantified Zika virus titers in human semen, the LoD achieved herein is well below the levels of virus found empirically in the field. A study in The Lancet (Vol 16, April 2016, page 405) established a viral load of $1\times10^{8.6}$ copies per ml (~$4\times10^8$) in semen, collected two weeks after diagnosis. Surprisingly, the viral load in the semen was roughly 100,000 times the titer found in the blood or urine during the symptomatic phase. Another report showed Zika titers of $2.9\times10^7$ and $1.1\times10^7$ copies/mL in the first and second semen samples, respectively, while the titers in urine were 4-orders of magnitude lower at $3.8\times10^3$ copies/mL, suggesting either replicative virus in seminal fluid or a mechanism of transport from blood that concentrates virus in the testis. (Emerging Infectious Diseases•www.cdc.gov/eid•Vol. 21, No. 2, February 2015, page 359-361.)

These data suggest that Zika viral titers in semen in natural infections may range from one to one hundred million (1-100$\times10^6$) copies per mL at the upper limit, to several orders of magnitude below $1\times10^6$ at the lower limit. In this context, an LoD at $2\times10^3$ GCE/mL should capture both the high viral titers observed in the current literature as well as 3-orders of magnitude below this value. An assay of this level of sensitivity will be valuable for the detection of low viral titers either during early-stage infection, but more importantly, virus levels during the post-symptom time period when viral replication is waning, but where viral reservoirs are still present and declining only slowly over time. A highly sensitive assay coupled with high specificity will be critical for determining a point in time when a negative rRT-PCR test result will indicate absence of virus with a high degree of confidence: a key factor for the public health goal of reducing or eliminating transmission of a devastating, teratogenic virus to a growing fetus.

With this in mind, contrived positive samples were constructed covering LoD and viral titers approaching levels found in natural semen infections (~$2\times10^7$). As of this date, we did not find any natural positives within the Brazilian or the travel-excluded US specimens, but attempts to procure semen from Zika positive individuals are ongoing. Any assistance that the CDC or FDA could provide in this regard would be greatly appreciated. For contrived positive samples, 60 semen specimens spiked with live virus, extracted viral RNA or synthetic RNA template have been tested with a score of 60/60 achieved. For contrived samples at or approaching the LoD, the synthetic RNA template was used due to the accuracy of the genome copy equivalents ("GCE") per mL viral inputs.

Table 10 shows an example of a blinded study using 200-uL whole semen. The contrived positives contain Zika RNA input ranging from $2\times10^7$ to $2\times10^5$ GCE/mL to simulate viral titers found in natural positive specimens as reported in current literature. Six negatives and six positive samples were used and run in duplicate.

TABLE 10

| # | Sample name | Titer added (GCE/mL) | FAM Ct | TET Ct |
|---|---|---|---|---|
| 1 | Semen RNA 1 | No virus added | 0 | 29.21 |
| 2 | Semen RNA 1 | No virus added | 0 | 28.98 |
| 3 | Semen RNA 2 | $2\times10^7$ | 21.95 | 36.87 |
| 4 | Semen RNA 2 | $2\times10^7$ | 22.29 | 34.33 |
| 5 | Semen RNA 3 | No virus added | 0 | 30.29 |
| 6 | Semen RNA 3 | No virus added | 0 | 31.15 |
| 7 | Semen RNA 4 | $2\times10^6$ | 26.07 | 29.52 |
| 8 | Semen RNA 4 | $2\times10^6$ | 26.09 | 29.82 |
| 9 | Semen RNA 5 | $2\times10^6$ | 25.53 | 33.40 |
| 10 | Semen RNA 5 | $2\times10^6$ | 26.47 | 30.35 |
| 11 | Semen RNA 6 | No virus added | 0 | 31.39 |
| 12 | Semen RNA 6 | No virus added | 0 | 30.51 |
| 13 | Semen RNA 7 | No virus added | 0 | 28.56 |
| 14 | Semen RNA 7 | No virus added | 0 | 28.16 |
| 15 | Semen RNA 8 | $2\times10^5$ | 29.62 | 29.74 |
| 16 | Semen RNA 8 | $2\times10^5$ | 29.96 | 29.47 |
| 17 | Semen RNA 9 | No virus added | 0 | 28.23 |
| 18 | Semen RNA 9 | No virus added | 0 | 28.55 |
| 19 | Semen RNA 10 | $2\times10^7$ | 21.92 | 37.56 |
| 20 | Semen RNA 10 | $2\times10^7$ | 21.88 | 34.73 |
| 21 | Semen RNA 11 | $2\times10^6$ | 25.93 | 33.45 |
| 22 | Semen RNA 11 | $2\times10^6$ | 25.46 | 32.56 |
| 23 | Semen RNA 12 | No virus added | 0 | 29.64 |
| 24 | Semen RNA 12 | No virus added | 0 | 29.55 |
| 25 | NTC | — | 0 | 0 |
| 26 | NTC | — | 0 | 0 |
| 27 | Zika Positive control | $2\times10^5$ GCE/rxn | 27.34 | 0 |
| 28 | Zika Positive control | $2\times10^5$ GCE/rxn | 27.26 | 0 |
| 29 | Human RNA control-beta-actin mRNA | — | 0 | 31.51 |
| 30 | Human RNA control-beta-actin mRNA | — | 0 | 31.61 |

An additional rRT-PCR was performed for a set of 14 contrived positive semen samples covering a titer range of $2\times10^9$ to $2\times10^3$ GCE/mL (6-orders of magnitude) with Ct values from 14-38.

In total, 78 negatives and 60 positives were tested after completion of serial dilution and LoD studies and summarized below in Table 11; high titers ($2\times10^7$ or greater GCE/mL), Moderate titers ($2\times10^5$-$2\times10^6$ GCE/mL), low titers (2,000-20,000 GCE/mL).

TABLE 11

| Template | High titers (tested/ positive) | Moderate titers (tested/ positive) | Low titers (tested/ positive) | Negatives (tested/ negative) |
|---|---|---|---|---|
| Zika | 10/10 | 40/40 | 10/10 | 478/478 |
| ATCB mRNA (IC) | 10/10 | 40/40 | 10/10 | 538/538 |
| NTC | negative | negative | negative | negative |

Use of the GIVF-ZIKV for testing of semen may be useful in men recovering from a Zika infection to confirm when it is safe to attempt conception. Alternatively, in asymptomatic men exposed to Zika after travel to an area of active infection, the GIVF-ZIKV Zika Virus RNA Qualitative Real-Time RT-PCR in semen test may be used after return to confirm the absence of infection and that conception can be considered. Finally, if the US experiences local transmission of Zika virus, direct testing of fresh or stored semen will provide superior information regarding the risk of infection compared to enzyme linked immunoassays which can indicate exposure, but is not helpful in determining the infectivity of semen.

Example 3

Results for Zika Virus Detection Using the 91-bp Amplicon

In this example, results for Zika virus detection using the 91-bp amplicon are shown. Briefly, using the materials and methods in Example 1, the 91-bp amplicon is targeted using SEQ ID NOs: 4-6.

Table 12 shows purified viral RNA to determine reactivity. Live virus and viral RNA were obtained from Health Department of England (HDE). The stock concentration/titer of purified viral RNA was 20 million genome copies per mL; $2\times10^7$ copies/mL. Dilution was over the stock. Target: Zika viral RNA NS5 gene 91-bp amplicon.

TABLE 12

| | Zika NS5 | | |
|---|---|---|---|
| Concentration: ZKV RNA | [FAM] Ct | Threshold Value | Experiment # |
| RNA HDE $10^{-1}$ dilution | 17.54 | 30 | ZKV_PCR88_HDE_RNA (No Ba) |
| RNA HDE $10^{-1}$ dilution | 17.17 | 30 | ZKV_PCR88_HDE_RNA (No Ba) |
| RNA HDE $10^{-1}$ dilution | 17.81 | 30 | ZKV_PCR89_HDE_RNA |
| RNA HDE $10^{-1}$ dilution | 17.55 | 30 | ZKV_PCR89_HDE_RNA |
| RNA HDE $10^{-1}$ dilution | 15.93 | 30 | ZKV_PCR91_HDE_RNA_1 |
| RNA HDE $10^{-1}$ dilution | 15.78 | 30 | ZKV_PCR91_HDE_RNA_1 |
| RNA HDE $10^{-2}$ dilution | 20.41 | 30 | ZKV_PCR88_HDE_RNA (No Ba) |
| RNA HDE $10^{-2}$ dilution | 20.65 | 30 | ZKV_PCR88_HDE_RNA (No Ba) |
| RNA HDE $10^{-2}$ dilution | 20.61 | 30 | ZKV_PCR89_HDE_RNA |
| RNA HDE $10^{-2}$ dilution | 20.94 | 30 | ZKV_PCR89_HDE_RNA |
| RNA HDE $10^{-2}$ dilution | 19.21 | 30 | ZKV_PCR91_HDE_RNA_1 |
| RNA HDE $10^{-2}$ dilution | 19.36 | 30 | ZKV_PCR91_HDE_RNA_1 |
| RNA HDE $10^{-3}$ dilution | 23.66 | 30 | ZKV_PCR88_HDE_RNA (No Ba) |
| RNA HDE $10^{-3}$ dilution | 23.87 | 30 | ZKV_PCR88_HDE_RNA (No Ba) |
| RNA HDE $10^{-3}$ dilution | 26.07 | 30 | ZKV_PCR89_HDE_RNA |
| RNA HDE $10^{-3}$ dilution | 26.71 | 30 | ZKV_PCR89_HDE_RNA |
| RNA HDE $10^{-3}$ dilution | 22.6 | 30 | ZKV_PCR91_HDE_RNA_1 |
| RNA HDE $10^{-3}$ dilution | 22.73 | 30 | ZKV_PCR91_HDE_RNA_1 |
| RNA HDE $10^{-4}$ dilution | 27.15 | 30 | ZKV_PCR88_HDE_RNA (No Ba) |
| RNA HDE $10^{-4}$ dilution | 27.31 | 30 | ZKV_PCR88_HDE_RNA (No Ba) |
| RNA HDE $10^{-4}$ dilution | 29.16 | 30 | ZKV_PCR89_HDE_RNA |
| RNA HDE $10^{-4}$ dilution | 28.56 | 30 | ZKV_PCR89_HDE_RNA |
| RNA HDE $10^{-4}$ dilution | 26.26 | 30 | ZKV_PCR91_HDE_RNA_1 |
| RNA HDE $10^{-4}$ dilution | 26.21 | 30 | ZKV_PCR91_HDE_RNA_1 |
| RNA HDE $10^{-5}$ dilution | 30.5 | 30 | ZKV_PCR88_HDE_RNA (No Ba) |
| RNA HDE $10^{-5}$ dilution | 31.23 | 30 | ZKV_PCR88_HDE_RNA (No Ba) |
| RNA HDE $10^{-5}$ dilution | 32.44 | 30 | ZKV_PCR89_HDE_RNA |
| RNA HDE $10^{-5}$ dilution | 32.39 | 30 | ZKV_PCR89_HDE_RNA |
| RNA HDE $10^{-5}$ dilution | 30.15 | 30 | ZKV_PCR91_HDE_RNA_1 |
| RNA HDE $10^{-5}$ dilution | 29.84 | 30 | ZKV_PCR91_HDE_RNA_1 |
| RNA HDE $10^{-6}$ dilution | 34.36 | 30 | ZKV_PCR88_HDE_RNA (No Ba) |
| RNA HDE $10^{-6}$ dilution | 34.92 | 30 | ZKV_PCR88_HDE_RNA (No Ba) |
| RNA HDE $10^{-6}$ dilution | 37.22 | 30 | ZKV_PCR89_HDE_RNA |
| RNA HDE $10^{-6}$ dilution | 36.42 | 30 | ZKV_PCR89_HDE_RNA |
| RNA HDE $10^{-6}$ dilution | 33.51 | 30 | ZKV_PCR91_HDE_RNA_1 |
| RNA HDE $10^{-6}$ dilution | 33.47 | 30 | ZKV_PCR91_HDE_RNA_1 |
| RNA HDE $10^{-7}$ dilution | 39.37 | 30 | ZKV_PCR88_HDE_RNA (No Ba) |
| RNA HDE $10^{-7}$ dilution | 38.17 | 30 | ZKV_PCR88_HDE_RNA (No Ba) |
| RNA HDE $10^{-7}$ dilution | 39.55 | 30 | ZKV_PCR89_HDE_RNA |
| RNA HDE $10^{-7}$ dilution | 39.63 | 30 | ZKV_PCR89_HDE_RNA |
| RNA HDE $10^{-7}$ dilution | 36.9 | 30 | ZKV_PCR91_HDE_RNA_1 |
| RNA HDE $10^{-7}$ dilution | 36.8 | 30 | ZKV_PCR91_HDE_RNA_1 |
| RNA HDE $10^{-8}$ dilution | 0 | 30 | ZKV_PCR88_HDE_RNA (No Ba) |
| RNA HDE $10^{-8}$ dilution | 0 | 30 | ZKV_PCR88_HDE_RNA (No Ba) |
| RNA HDE $10^{-8}$ dilution | 0 | 30 | ZKV_PCR89_HDE_RNA |
| RNA HDE $10^{-8}$ dilution | 0 | 30 | ZKV_PCR89_HDE_RNA |

TABLE 12-continued

| | Zika NS5 | | |
|---|---|---|---|
| Concentration: ZKV RNA | [FAM] Ct | Threshold Value | Experiment # |
| RNA HDE $10^{-8}$ dilution | 0 | 30 | ZKV_PCR91_HDE_RNA_1 |
| RNA HDE $10^{-8}$ dilution | 0 | 30 | ZKV_PCR91_HDE_RNA_1 |
| RNA HDE $10^{-9}$ dilution | 0 | 30 | ZKV_PCR91_HDE_RNA_1 |
| RNA HDE $10^{-9}$ dilution | 0 | 30 | ZKV_PCR91_HDE_RNA_1 |
| RNA HDE $10^{-10}$ dilution | 0 | 30 | ZKV_PCR91_HDE_RNA_1 |
| RNA HDE $10^{-10}$ dilution | 0 | 30 | ZKV_PCR91_HDE_RNA_1 |

Limit of Detection (LOD) using viral RNA was 2 copies per mL at the $10^{-7}$ dilution point.

Table 13 shows the results of testing Zika viral RNA in human total nucleic acids (RNA and DNA combined) extracted from either blood or semen to determine detection of Zika in a background of human nucleic acid. These reactions are multiplex RT-PCR including primer/probe sets for Zika viral RNA NS5 gene 91-bp amplicon and beta-actin mRNA (human positive internal control, IC). Each reaction contained 1 uL of viral RNA and 4 uL of human total nucleic acid from either blood or semen, as indicated. The stock concentration/titer of purified viral RNA was 20 million genome copies per mL; $2\times10^7$ copies/mL. Dilution was over the stock.

TABLE 13

| | Zika NS5 | | | beta-actin mRNA | | |
|---|---|---|---|---|---|---|
| Concentration: ZKV RNA | [FAM] Ct | Threshold Value | Experiment # | [TET] Ct | Threshold Value | Experiment # |
| Zika RNA HDE + Blood RNA/DNA | | | | | | |
| RNA HDE $10^{-1}$ dilution + Blood RNA/DNA | 15.52 | 30 | ZKV_PCR91_HDE_RNA_5 | 0 | 30 | ZKV_PCR91_HDE_RNA_5 |
| RNA HDE $10^{-1}$ dilution + Blood RNA/DNA | 15.45 | 30 | ZKV_PCR91_HDE_RNA_5 | 0 | 30 | ZKV_PCR91_HDE_RNA_5 |
| RNA HDE $10^{-2}$ dilution + Blood RNA/DNA | 18.73 | 30 | ZKV_PCR91_HDE_RNA_5 | 0 | 30 | ZKV_PCR91_HDE_RNA_5 |
| RNA HDE $10^{-2}$ dilution + Blood RNA/DNA | 19.21 | 30 | ZKV_PCR91_HDE_RNA_5 | 0 | 30 | ZKV_PCR91_HDE_RNA_5 |
| RNA HDE $10^{-3}$ dilution + Blood RNA/DNA | 23.11 | 30 | ZKV_PCR91_HDE_RNA_5 | 0 | 30 | ZKV_PCR91_HDE_RNA_5 |
| RNA HDE $10^{-3}$ dilution + Blood RNA/DNA | 22.94 | 30 | ZKV_PCR91_HDE_RNA_5 | 0 | 30 | ZKV_PCR91_HDE_RNA_5 |
| RNA HDE $10^{-4}$ dilution + Blood RNA/DNA | 26.17 | 30 | ZKV_PCR91_HDE_RNA_5 | 31.89 | 30 | ZKV_PCR91_HDE_RNA_5 |
| RNA HDE $10^{-4}$ dilution + Blood RNA/DNA | 26.53 | 30 | ZKV_PCR91_HDE_RNA_5 | 36.37 | 30 | ZKV_PCR91_HDE_RNA_5 |
| RNA HDE $10^{-5}$ dilution + Blood RNA/DNA | 29.9 | 30 | ZKV_PCR91_HDE_RNA_5 | 32.27 | 30 | ZKV_PCR91_HDE_RNA_5 |
| RNA HDE $10^{-5}$ dilution + Blood RNA/DNA | 29.19 | 30 | ZKV_PCR91_HDE_RNA_5 | 30.87 | 30 | ZKV_PCR91_HDE_RNA_5 |
| RNA HDE $10^{-6}$ dilution + Blood RNA/DNA | 0 | 30 | ZKV_PCR91_HDE_RNA_5 | 30.64 | 30 | ZKV_PCR91_HDE_RNA_5 |
| RNA HDE $10^{-6}$ dilution + Blood RNA/DNA | 32.84 | 30 | ZKV_PCR91_HDE_RNA_5 | 30.32 | 30 | ZKV_PCR91_HDE_RNA_5 |
| RNA HDE $10^{-7}$ dilution + Blood RNA/DNA | 36.92 | 30 | ZKV_PCR91_HDE_RNA_5 | 30.21 | 30 | ZKV_PCR91_HDE_RNA_5 |
| RNA HDE $10^{-7}$ dilution + Blood RNA/DNA | 38.47 | 30 | ZKV_PCR91_HDE_RNA_5 | 30.21 | 30 | ZKV_PCR91_HDE_RNA_5 |
| Zika RNA HDE + Semen RNA/DNA | | | | | | |
| RNA HDE $10^{-2}$ dilution + Semen RNA/DNA | 21.15 | 30 | ZKV_PCR92_HDE_RNA | 44.6 | 30 | ZKV_PCR92_HDE_RNA |

TABLE 13-continued

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| RNA HDE $10^{-2}$ dilution + Semen RNA/DNA | 21.25 | 30 | ZKV_PCR92_HDE_RNA | 34.68 | 30 | ZKV_PCR92_HDE_RNA |
| RNA HDE $10^{-3}$ dilution + Semen RNA/DNA | 24.63 | 30 | ZKV_PCR92_HDE_RNA | 29.63 | 30 | ZKV_PCR92_HDE_RNA |
| RNA HDE $10^{-3}$ dilution + Semen RNA/DNA | 25.22 | 30 | ZKV_PCR92_HDE_RNA | 28.58 | 30 | ZKV_PCR92_HDE_RNA |
| RNA HDE $10^{-4}$ dilution + Semen RNA/DNA | 29.05 | 30 | ZKV_PCR92_HDE_RNA | 28.58 | 30 | ZKV_PCR92_HDE_RNA |
| RNA HDE $10^{-4}$ dilution + Semen RNA/DNA | 28.56 | 30 | ZKV_PCR92_HDE_RNA | 28.72 | 30 | ZKV_PCR92_HDE_RNA |
| RNA HDE $10^{-5}$ dilution + Semen RNA/DNA | 32.58 | 30 | ZKV_PCR92_HDE_RNA | 29.26 | 30 | ZKV_PCR92_HDE_RNA |
| RNA HDE $10^{-5}$ dilution + Semen RNA/DNA | 33.1 | 30 | ZKV_PCR92_HDE_RNA | 28.72 | 30 | ZKV_PCR92_HDE_RNA |
| RNA HDE $10^{-6}$ dilution + Semen RNA/DNA | 37.8 | 30 | ZKV_PCR92_HDE_RNA | 28.23 | 30 | ZKV_PCR92_HDE_RNA |
| RNA HDE $10^{-6}$ dilution + Semen RNA/DNA | 37.71 | 30 | ZKV_PCR92_HDE_RNA | 28.45 | 30 | ZKV_PCR92_HDE_RNA |
| RNA HDE $10^{-7}$ dilution + Semen RNA/DNA | 45.61 | 30 | ZKV_PCR92_HDE_RNA | 28.47 | 30 | ZKV_PCR92_HDE_RNA |
| RNA HDE $10^{-7}$ dilution + Semen RNA/DNA | 40.29 | 30 | ZKV_PCR92_HDE_RNA | 28.09 | 30 | ZKV_PCR92_HDE_RNA |

Limit of Detection (LOD) using viral RNA in a background of blood or semen total nucleic acid (RNA/DNA) was 2 copies per mL at the $10^{-7}$ dilution point.

Table 14 used 1) RNA extracted from live Zika virus using described extraction protocol and spiked into total human nucleic acid (RNA/DNA) extracted from blood, and 2) RNA extracted from live Zika virus using described extraction protocol and added directly to total human nucleic acid (RNA/DNA) extracted from semen and tested via multiplex RT-PCR using the described protocol. These assays are used to determine the detection of live Zika virus extracted in a background of human nucleic acid (RNA/DNA). These reactions are multiplex RT-PCR including primer/probe sets for Zika viral RNA NS5 gene 91-bp amplicon and beta-actin mRNA (human positive internal control, IC). The stock concentration of live Zika virus was 200 million viral particles per mL; $2\times10^8$ virons/mL. This corresponds to $2\times10^6$ Plaque Forming Units (PFU, 100 virus particles generate 1 PFU for this strain). Each reaction for contained 1 uL of viral RNA (at indicated dilution over the stock) and 4 uL of total nucleic acid from human blood or semen.

TABLE 14

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| Zika Live Virus + Blood RNA/DNA | | | | | | |
| Zika $10^{-5}$ dilution + Blood RNA/DNA | 29.11 | 30 | ZKV_PCR93_2 | 28.13 | 30 | ZKV_PCR93_2 |
| Zika $10^{-5}$ dilution + Blood RNA/DNA | 28.67 | 30 | ZKV_PCR93_2 | 27.64 | 30 | ZKV_PCR93_2 |
| Zika $10^{-6}$ dilution + Blood RNA/DNA | 32.39 | 30 | ZKV_PCR93_2 | 27.59 | 30 | ZKV_PCR93_2 |
| Zika $10^{-6}$ dilution + Blood RNA/DNA | 32.52 | 30 | ZKV_PCR93_2 | 27.86 | 30 | ZKV_PCR93_2 |
| Zika $10^{-7}$ dilution + Blood RNA/DNA | 37.35 | 30 | ZKV_PCR93_2 | 30.41 | 30 | ZKV_PCR93_2 |
| Zika $10^{-7}$ dilution + Blood RNA/DNA | 38.1 | 30 | ZKV_PCR93_2 | 30.46 | 30 | ZKV_PCR93_2 |
| Zika $10^{-8}$ dilution + Blood RNA/DNA | 42.66 | 30 | ZKV_PCR93_2 | 31.34 | 30 | ZKV_PCR93_2 |

TABLE 14-continued

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| Zika $10^{-8}$ dilution + Blood RNA/DNA | 0 | 30 | ZKV_PCR93_2 | 31.5 | 30 | ZKV_PCR93_2 |
| Zika $10^{-9}$ dilution + Blood RNA/DNA | 0 | 30 | ZKV_PCR93_2 | 27.3 | 30 | ZKV_PCR93_2 |
| Zika $10^{-9}$ dilution + Blood RNA/DNA | 0 | 30 | ZKV_PCR93_2 | 27.23 | 30 | ZKV_PCR93_2 |
| Zika Live Virus + Semen RNA/DNA | | | | | | |
| Zika $10^{-1}$ dilution + Semen RNA/DNA | 23.13 | 30 | ZKV_PCR94 | 34.95 | 30 | ZKV_PCR94 |
| Zika $10^{-1}$ dilution + Semen RNA/DNA | 22.79 | 30 | ZKV_PCR94 | 32.85 | 30 | ZKV_PCR94 |
| Zika $10^{-1}$ dilution + Semen RNA/DNA | 22.57 | 30 | ZKV_PCR94 | 32.64 | 30 | ZKV_PCR94 |
| Zika $10^{-2}$ dilution + Semen RNA/DNA | 26.94 | 30 | ZKV_PCR94 | 30.5 | 30 | ZKV_PCR94 |
| Zika $10^{-2}$ dilution + Semen RNA/DNA | 26.98 | 30 | ZKV_PCR94 | 30.28 | 30 | ZKV_PCR94 |
| Zika $10^{-2}$ dilution + Semen RNA/DNA | 26.57 | 30 | ZKV_PCR94 | 29.84 | 30 | ZKV_PCR94 |
| Zika $10^{-3}$ dilution + Semen RNA/DNA | 32.47 | 30 | ZKV_PCR94 | 28.7 | 30 | ZKV_PCR94 |
| Zika $10^{-3}$ dilution + Semen RNA/DNA | 32.16 | 30 | ZKV_PCR94 | 28.55 | 30 | ZKV_PCR94 |
| Zika $10^{-3}$ dilution + Semen RNA/DNA | 31.76 | 30 | ZKV_PCR94 | 28.53 | 30 | ZKV_PCR94 |
| Zika $10^{-4}$ dilution + Semen RNA/DNA | 34.66 | 30 | ZKV_PCR94 | 28.47 | 30 | ZKV_PCR94 |
| Zika $10^{-4}$ dilution + Semen RNA/DNA | 34.59 | 30 | ZKV_PCR94 | 27.72 | 30 | ZKV_PCR94 |
| Zika $10^{-4}$ dilution + Semen RNA/DNA | 35.35 | 30 | ZKV_PCR94 | 28.2 | 30 | ZKV_PCR94 |
| Zika $10^{-5}$ dilution + Semen RNA/DNA | 0 | 30 | ZKV_PCR94 | 31.35 | 30 | ZKV_PCR94 |
| Zika $10^{-5}$ dilution + Semen RNA/DNA | 41.81 | 30 | ZKV_PCR94 | 31.39 | 30 | ZKV_PCR94 |
| Zika $10^{-5}$ dilution + Semen RNA/DNA | 41.74 | 30 | ZKV_PCR94 | 31.5 | 30 | ZKV_PCR94 |
| Zika $10^{-6}$ dilution + Semen RNA/DNA | 0 | 30 | ZKV_PCR94 | 32.82 | 30 | ZKV_PCR94 |
| Zika $10^{-6}$ dilution + Semen RNA/DNA | 0 | 30 | ZKV_PCR94 | 32.43 | 30 | ZKV_PCR94 |
| Zika $10^{-6}$ dilution + Semen RNA/DNA | 0 | 30 | ZKV_PCR94 | 31.83 | 30 | ZKV_PCR94 |
| Zika $10^{-7}$ dilution + Semen RNA/DNA | 0 | 30 | ZKV_PCR94 | 30.91 | 30 | ZKV_PCR94 |
| Zika $10^{-7}$ dilution + Semen RNA/DNA | 0 | 30 | ZKV_PCR94 | 31.22 | 30 | ZKV_PCR94 |
| Zika $10^{-7}$ dilution + Semen RNA/DNA | 0 | 30 | ZKV_PCR94 | 31.35 | 30 | ZKV_PCR94 |
| Zika $10^{-8}$ dilution + Semen RNA/DNA | 0 | 30 | ZKV_PCR94 | 31.25 | 30 | ZKV_PCR94 |
| Zika $10^{-8}$ dilution + Semen RNA/DNA | 0 | 30 | ZKV_PCR94 | 31.51 | 30 | ZKV_PCR94 |
| Zika $10^{-8}$ dilution + Semen RNA/DNA | 0 | 30 | ZKV_PCR94 | 31.15 | 30 | ZKV_PCR94 |

Limit of Detection (LOD) using live virus extracted for total nucleic acids (RNA/DNA) from whole human semen will be established in following studies.

Table 15 used intact live Zika virus added directly to whole human semen and extracted for total nucleic acid (RNA/DNA) and tested via multiplex RT-PCR using the described protocol. These assays are used to determine the detection of live Zika virus in human semen extracted for total nucleic acid (RNA/DNA) and establish Limitation of Detection (LOD) for semen samples. These reactions are multiplex RT-PCR including primer/probe sets for Zika and beta-actin mRNA (human positive internal control, IC). The stock concentration of live Zika virus was 200 million viral particles per mL; $2\times10^{8}$ virons/mL. This corresponds to $2\times10^{6}$ Plaque Forming Units (PFU, 100 virus particles generate 1 PFU for this strain). Twenty uL of live virus from stock and at each dilution point was added to 180 uL of whole semen and extracted according to protocol presented herein. Since 20 uL in 200 uL constituents a 1:10 dilution, the highest titer that can be tested in semen is $2\times10^{7}$ virons/mL. This added 1:10-dilution is incorporated into Table 15 below.

TABLE 15

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| Zika Live Virus + Semen | | | | | | |
| Zika $10^{-4}$ dilution + Semen | 37.81 | 30 | ZKV_PCR96 | 30.34 | 30 | ZKV_PCR96 |
| Zika $10^{-4}$ dilution + Semen | 37.13 | 30 | ZKV_PCR96 | 30.11 | 30 | ZKV_PCR96 |
| Zika $10^{-4}$ dilution + Semen | 38.4 | 30 | ZKV_PCR96 | 30.23 | 30 | ZKV_PCR96 |
| Zika $10^{-4}$ dilution + Semen | 37.51 | 30 | ZKV_PCR96 | 31.1 | 30 | ZKV_PCR96 |
| Zika $10^{-4}$ dilution + Semen | 40.88 | 30 | ZKV_PCR96 | 30.5 | 30 | ZKV_PCR96 |
| Zika $10^{-4}$ dilution + Semen | 37.79 | 30 | ZKV_PCR96 | 30.21 | 30 | ZKV_PCR96 |
| Zika $10^{-4}$ dilution + Semen | 38.36 | 30 | ZKV_PCR96 | 28.07 | 30 | ZKV_PCR96 |
| Zika $10^{-4}$ dilution + Semen | 39 | 30 | ZKV_PCR96 | 28.97 | 30 | ZKV_PCR96 |
| Zika $10^{-4}$ dilution + Semen | 39.36 | 30 | ZKV_PCR96 | 28 | 30 | ZKV_PCR96 |
| Zika $10^{-4}$ dilution + Semen | 37.61 | 30 | ZKV_PCR96 | 30.79 | 30 | ZKV_PCR96 |
| Zika $10^{-4}$ dilution + Semen | 38.3 | 30 | ZKV_PCR96 | 29.7 | 30 | ZKV_PCR96 |
| Zika $10^{-4}$ dilution + Semen | 37.22 | 30 | ZKV_PCR96 | 29.56 | 30 | ZKV_PCR96 |
| Zika $10^{-4}$ dilution + Semen | 36.05 | 30 | ZKV_PCR96 | 28.14 | 30 | ZKV_PCR96 |
| Zika $10^{-4}$ dilution + Semen | 36.37 | 30 | ZKV_PCR96 | 28.54 | 30 | ZKV_PCR96 |
| Zika $10^{-4}$ dilution + Semen | 36.14 | 30 | ZKV_PCR96 | 28.53 | 30 | ZKV_PCR96 |
| Zika $10^{-5}$ dilution + Semen | 0 | 30 | ZKV_PCR96 | 28.43 | 30 | ZKV_PCR96 |
| Zika $10^{-5}$ dilution + Semen | 40.66 | 30 | ZKV_PCR96 | 28.16 | 30 | ZKV_PCR96 |
| Zika $10^{-5}$ dilution + Semen | 0 | 30 | ZKV_PCR96 | 28.11 | 30 | ZKV_PCR96 |
| Zika $10^{-5}$ dilution + Semen | 38.64 | 30 | ZKV_PCR96 | 30.14 | 30 | ZKV_PCR96 |
| Zika $10^{-5}$ dilution + Semen | 0 | 30 | ZKV_PCR96 | 30.81 | 30 | ZKV_PCR96 |
| Zika $10^{-5}$ dilution + Semen | 0 | 30 | ZKV_PCR96 | 30.54 | 30 | ZKV_PCR96 |
| Zika $10^{-5}$ dilution + Semen | 43.12 | 30 | ZKV_PCR96 | 29.48 | 30 | ZKV_PCR96 |
| Zika $10^{-5}$ dilution + Semen | 43.22 | 30 | ZKV_PCR96 | 30.77 | 30 | ZKV_PCR96 |
| Zika $10^{-5}$ dilution + Semen | 44.81 | 30 | ZKV_PCR96 | 30.49 | 30 | ZKV_PCR96 |
| Zika $10^{-5}$ dilution + Semen | 38.96 | 30 | ZKV_PCR96 | 30.95 | 30 | ZKV_PCR96 |
| Zika $10^{-5}$ dilution + Semen | 0 | 30 | ZKV_PCR96 | 30.98 | 30 | ZKV_PCR96 |
| Zika $10^{-5}$ dilution + Semen | 39.28 | 30 | ZKV_PCR96 | 31.07 | 30 | ZKV_PCR96 |
| Zika $10^{-5}$ dilution + Semen | 0 | 30 | ZKV_PCR96 | 30 | 30 | ZKV_PCR96 |
| Zika $10^{-5}$ dilution + Semen | 0 | 30 | ZKV_PCR96 | 30.35 | 30 | ZKV_PCR96 |
| Zika $10^{-5}$ dilution + Semen | 0 | 30 | ZKV_PCR96 | 29.94 | 30 | ZKV_PCR96 |

Based on these studies using live virus extracted for total nucleic acids (RNA/DNA) from human semen indicates that the LOD is between the 200 and 2,000 viruses/mL ($1 \times 10^{-5}$ and $1 \times 10^{-4}$ dilution points).

Table 16 used intact live Zika virus added directly to whole human semen and extracted for total nucleic acid (RNA/DNA) and tested via multiplex RT-PCR using the described protocol. These assays are used to determine the detection of live Zika virus in human semen extracted for total nucleic acid (RNA/DNA) and establish LOD for semen samples. These reactions are multiplex RT-PCR including primer/probe sets for Zika and beta-actin mRNA (human positive internal control, IC). The concentration of live Zika virus was 200 million viral particles per mL; $2 \times 10^8$ virons/mL. This corresponds to $2 \times 10^6$ Plaque Forming Units (PFU, 100 virus particles generate 1 PFU for this strain). Twenty uL of live virus at each dilution point was added to 180 uL of whole semen and extracted according to protocol presented herein. Since 20 uL in 200 uL constituents a 1:10 dilution, the highest titer that can be tested in semen is $2 \times 10^7$ virons/mL. This added 1:10 dilution is incorporated into Table 16 below.

TABLE 16

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| $10^{-1}$ dilution | 21.25 | 30 | ZKV_PCR101A | 35.87 | 30 | ZKV_PCR101A |
| $10^{-1}$ dilution | 21.1 | 30 | ZKV_PCR101A | 32.65 | 30 | ZKV_PCR101A |
| $10^{-1}$ dilution | 20.69 | 30 | ZKV_PCR101A | 33.98 | 30 | ZKV_PCR101A |
| $10^{-1}$ dilution | 23.03 | 30 | ZKV_PCR101A | 33.49 | 30 | ZKV_PCR101A |
| $10^{-1}$ dilution | 23.27 | 30 | ZKV_PCR101A | 30.36 | 30 | ZKV_PCR101A |
| $10^{-1}$ dilution | 22.85 | 30 | ZKV_PCR101A | 31.43 | 30 | ZKV_PCR101A |
| $10^{-1}$ dilution | 20.69 | 30 | ZKV_PCR101A | 45.04 | 30 | ZKV_PCR101A |
| $10^{-1}$ dilution | 21.21 | 30 | ZKV_PCR101A | 49.32 | 30 | ZKV_PCR101A |
| $10^{-1}$ dilution | 20.58 | 30 | ZKV_PCR101A | 44.91 | 30 | ZKV_PCR101A |
| $10^{-2}$ dilution | 25.33 | 30 | ZKV_PCR101A | 30.42 | 30 | ZKV_PCR101A |
| $10^{-2}$ dilution | 25.23 | 30 | ZKV_PCR101A | 31.47 | 30 | ZKV_PCR101A |
| $10^{-2}$ dilution | 25.64 | 30 | ZKV_PCR101A | 31.32 | 30 | ZKV_PCR101A |
| $10^{-2}$ dilution | 25.52 | 30 | ZKV_PCR101A | 29.08 | 30 | ZKV_PCR101A |
| $10^{-2}$ dilution | 25.44 | 30 | ZKV_PCR101A | 28.89 | 30 | ZKV_PCR101A |
| $10^{-2}$ dilution | 25.57 | 30 | ZKV_PCR101A | 28.99 | 30 | ZKV_PCR101A |
| $10^{-2}$ dilution | 25.15 | 30 | ZKV_PCR101A | 28.53 | 30 | ZKV_PCR101A |
| $10^{-2}$ dilution | 25.5 | 30 | ZKV_PCR101A | 28.46 | 30 | ZKV_PCR101A |
| $10^{-2}$ dilution | 25.78 | 30 | ZKV_PCR101A | 29.67 | 30 | ZKV_PCR101A |
| $10^{-3}$ dilution | 29.63 | 30 | ZKV_PCR101A | 29.53 | 30 | ZKV_PCR101A |
| $10^{-3}$ dilution | 29.91 | 30 | ZKV_PCR101A | 29.22 | 30 | ZKV_PCR101A |
| $10^{-3}$ dilution | 29.84 | 30 | ZKV_PCR101A | 29.29 | 30 | ZKV_PCR101A |
| $10^{-3}$ dilution | 29.24 | 30 | ZKV_PCR101A | 28.51 | 30 | ZKV_PCR101A |
| $10^{-3}$ dilution | 29.27 | 30 | ZKV_PCR101A | 29.7 | 30 | ZKV_PCR101A |
| $10^{-3}$ dilution | 29.81 | 30 | ZKV_PCR101A | 29.59 | 30 | ZKV_PCR101A |
| $10^{-3}$ dilution | 29.05 | 30 | ZKV_PCR101A | 28.34 | 30 | ZKV_PCR101A |
| $10^{-3}$ dilution | 28.58 | 30 | ZKV_PCR101A | 28.24 | 30 | ZKV_PCR101A |
| $10^{-3}$ dilution | 28.56 | 30 | ZKV_PCR101A | 28.17 | 30 | ZKV_PCR101A |
| $10^{-4}$ dilution | 34.86 | 30 | ZKV_PCR101A | 31.22 | 30 | ZKV_PCR101A |
| $10^{-4}$ dilution | 34.96 | 30 | ZKV_PCR101A | 31.48 | 30 | ZKV_PCR101A |
| $10^{-4}$ dilution | 34.6 | 30 | ZKV_PCR101A | 31.16 | 30 | ZKV_PCR101A |
| $10^{-4}$ dilution | 31.35 | 30 | ZKV_PCR101B | 28.67 | 30 | ZKV_PCR101B |
| $10^{-4}$ dilution | 31.41 | 30 | ZKV_PCR101B | 28.1 | 30 | ZKV_PCR101B |
| $10^{-4}$ dilution | 30.88 | 30 | ZKV_PCR101B | 28.06 | 30 | ZKV_PCR101B |
| $10^{-4}$ dilution | 31.18 | 30 | ZKV_PCR101B | 29.77 | 30 | ZKV_PCR101B |
| $10^{-4}$ dilution | 30.91 | 30 | ZKV_PCR101B | 29.39 | 30 | ZKV_PCR101B |
| $10^{-4}$ dilution | 30.74 | 30 | ZKV_PCR101B | 29.43 | 30 | ZKV_PCR101B |
| $5 \times 10^{-5}$ dilution | 0 | 30 | ZKV_PCR101B | 31.19 | 30 | ZKV_PCR101B |
| $5 \times 10^{-5}$ dilution | 33.28 | 30 | ZKV_PCR101B | 30.44 | 30 | ZKV_PCR101B |
| $5 \times 10^{-5}$ dilution | 32.57 | 30 | ZKV_PCR101B | 29.69 | 30 | ZKV_PCR101B |
| $5 \times 10^{-5}$ dilution | 32.36 | 30 | ZKV_PCR101B | 30.12 | 30 | ZKV_PCR101B |
| $5 \times 10^{-5}$ dilution | 32.41 | 30 | ZKV_PCR101B | 30.19 | 30 | ZKV_PCR101B |
| $5 \times 10^{-5}$ dilution | 32.46 | 30 | ZKV_PCR101B | 29.7 | 30 | ZKV_PCR101B |
| $5 \times 10^{-5}$ dilution | 31.72 | 30 | ZKV_PCR101B | 28.35 | 30 | ZKV_PCR101B |
| $5 \times 10^{-5}$ dilution | 31.83 | 30 | ZKV_PCR101B | 28.67 | 30 | ZKV_PCR101B |
| $5 \times 10^{-5}$ dilution | 32.43 | 30 | ZKV_PCR101B | 28.46 | 30 | ZKV_PCR101B |
| $2 \times 10^{-5}$ dilution | 32.51 | 30 | ZKV_PCR101B | 28.38 | 30 | ZKV_PCR101B |
| $2 \times 10^{-5}$ dilution | 33.7 | 30 | ZKV_PCR101B | 28.88 | 30 | ZKV_PCR101B |
| $2 \times 10^{-5}$ dilution | 33.6 | 30 | ZKV_PCR101B | 28.63 | 30 | ZKV_PCR101B |
| $2 \times 10^{-5}$ dilution | 33.68 | 30 | ZKV_PCR101B | 29.82 | 30 | ZKV_PCR101B |
| $2 \times 10^{-5}$ dilution | 33.51 | 30 | ZKV_PCR101B | 28.96 | 30 | ZKV_PCR101B |
| $2 \times 10^{-5}$ dilution | 33.99 | 30 | ZKV_PCR101B | 29.48 | 30 | ZKV_PCR101B |
| $2 \times 10^{-5}$ dilution | 33.15 | 30 | ZKV_PCR101B | 27.32 | 30 | ZKV_PCR101B |
| $2 \times 10^{-5}$ dilution | 33.49 | 30 | ZKV_PCR101B | 28.21 | 30 | ZKV_PCR101B |
| $2 \times 10^{-5}$ dilution | 35.13 | 30 | ZKV_PCR101B | 28.73 | 30 | ZKV_PCR101B |
| $10^{-5}$ dilution | 35.73 | 30 | ZKV_PCR101B | 28.83 | 30 | ZKV_PCR101B |
| $10^{-5}$ dilution | 35.15 | 30 | ZKV_PCR101B | 29.57 | 30 | ZKV_PCR101B |
| $10^{-5}$ dilution | 34.24 | 30 | ZKV_PCR101B | 28.36 | 30 | ZKV_PCR101B |
| $10^{-5}$ dilution | 34.5 | 30 | ZKV_PCR101B | 28.59 | 30 | ZKV_PCR101B |
| $10^{-5}$ dilution | 35.16 | 30 | ZKV_PCR101B | 28.93 | 30 | ZKV_PCR101B |
| $10^{-5}$ dilution | 34.79 | 30 | ZKV_PCR101B | 28.79 | 30 | ZKV_PCR101B |
| $10^{-5}$ dilution | 0 | 30 | ZKV_PCR101C | 30.13 | 30 | ZKV_PCR101C |
| $10^{-5}$ dilution | 0 | 30 | ZKV_PCR101C | 30.13 | 30 | ZKV_PCR101C |
| $10^{-5}$ dilution | 0 | 30 | ZKV_PCR101C | 30.23 | 30 | ZKV_PCR101C |
| Blank | 0 | 0 | ZKV_PCR101A | 0 | 0 | ZKV_PCR101A |
| Blank | 0 | 0 | ZKV_PCR101B | 0 | 0 | ZKV_PCR101B |
| Blank | 0 | 0 | ZKV_PCR101C | 0 | 0 | ZKV_PCR101C |

Table 17 used intact live Zika virus added directly to whole human semen and extracted for total nucleic acid (RNA/DNA) and tested via multiplex RT-PCR using the described protocol. These assays are used to determine the detection of live Zika virus in human semen extracted for total nucleic acid (RNA/DNA) and establish LOD for semen samples. These reactions are multiplex RT-PCR including primer/probe sets for Zika and beta-actin mRNA (human positive internal control, IC). The stock concentration of live Zika virus was 200 million viral particles per mL; $2 \times 10^8$ virons/mL. This corresponds to $2 \times 10^6$ Plaque Forming Units (PFU, 100 virus particles generate 1 PFU for this strain).

Twenty uL of live virus at each dilution point was added to 180 uL of whole semen and extracted according to protocol presented herein. Since 20 uL in 200 uL constituents a 1:10 dilution, the highest titer that can be tested in semen is $2\times10^7$ virons/mL. This added 1:10 dilution is incorporated into Table 17 below. A dilution value ($2\times10^{-5}$) of live virus corresponding to 400 viruses per mL of semen was used for multiple assays at this titer to test reproducibility at the LOD.

TABLE 17

| Concentration: ZKV RNA | Zika NS5 | | | beta-actin mRNA | | |
|---|---|---|---|---|---|---|
| | [FAM] Ct | Threshold Value | Experiment # | [TET] Ct | Threshold Value | Experiment # |
| PCR with No beta-actin | | | | | | |
| LOD ($2 \times 10^{-5}$ dilution) | 36.62 | 30 | ZKV_PCR98_NoBa | 0 | 30 | ZKV_PCR98_NoBa |
| LOD ($2 \times 10^{-5}$ dilution) | 35.56 | 30 | ZKV_PCR98_NoBa | 0 | 30 | ZKV_PCR98_NoBa |
| LOD ($2 \times 10^{-5}$ dilution) | 36.43 | 30 | ZKV_PCR98_NoBa | 0 | 30 | ZKV_PCR98_NoBa |
| LOD ($2 \times 10^{-5}$ dilution) | 35.02 | 30 | ZKV_PCR98_NoBa | 0 | 30 | ZKV_PCR98_NoBa |
| LOD ($2 \times 10^{-5}$ dilution) | 37.21 | 30 | ZKV_PCR98_NoBa | 0 | 30 | ZKV_PCR98_NoBa |
| LOD ($2 \times 10^{-5}$ dilution) | 36.07 | 30 | ZKV_PCR98_NoBa | 0 | 30 | ZKV_PCR98_NoBa |
| PCR with beta-actin | | | | | | |
| LOD ($2 \times 10^{-5}$ dilution) | 38.89 | 30 | ZKV_PCR98_2 | 28.19 | 30 | ZKV_PCR98_2 |
| LOD ($2 \times 10^{-5}$ dilution) | 40.49 | 30 | ZKV_PCR98_2 | 28.32 | 30 | ZKV_PCR98_2 |
| LOD ($2 \times 10^{-5}$ dilution) | 37.84 | 30 | ZKV_PCR98_2 | 27.87 | 30 | ZKV_PCR98_2 |
| LOD ($2 \times 10^{-5}$ dilution) | 41.87 | 30 | ZKV_PCR98_2 | 27.94 | 30 | ZKV_PCR98_2 |
| LOD ($2 \times 10^{-5}$ dilution) | 39.72 | 30 | ZKV_PCR98_2 | 27.53 | 30 | ZKV_PCR98_2 |
| LOD ($2 \times 10^{-5}$ dilution) | 41.25 | 30 | ZKV_PCR98_2 | 27.58 | 30 | ZKV_PCR98_2 |
| PCR with beta-actin | | | | | | |
| LOD ($2 \times 10^{-5}$ dilution) | 38.55 | 30 | ZKV_PCR99_1 | 28.49 | 30 | ZKV_PCR99_1 |
| LOD ($2 \times 10^{-5}$ dilution) | 40.53 | 30 | ZKV_PCR99_1 | 27.18 | 30 | ZKV_PCR99_1 |
| LOD ($2 \times 10^{-5}$ dilution) | 39.65 | 30 | ZKV_PCR99_1 | 27.72 | 30 | ZKV_PCR99_1 |
| LOD ($2 \times 10^{-5}$ dilution) | 41.16 | 30 | ZKV_PCR99_1 | 27.57 | 30 | ZKV_PCR99_1 |
| LOD ($2 \times 10^{-5}$ dilution) | 39.67 | 30 | ZKV_PCR99_1 | 28.14 | 30 | ZKV_PCR99_1 |
| LOD ($2 \times 10^{-5}$ dilution) | 39.28 | 30 | ZKV_PCR99_1 | 27.67 | 30 | ZKV_PCR99_1 |
| LOD ($2 \times 10^{-5}$ dilution) | 40.33 | 30 | ZKV_PCR99_1 | 27.73 | 30 | ZKV_PCR99_1 |
| LOD ($2 \times 10^{-5}$ dilution) | 40.8 | 30 | ZKV_PCR99_1 | 27.2 | 30 | ZKV_PCR99_1 |
| LOD ($2 \times 10^{-5}$ dilution) | 42.12 | 30 | ZKV_PCR99_1 | 27.2 | 30 | ZKV_PCR99_1 |
| LOD ($2 \times 10^{-5}$ dilution) | 39.12 | 30 | ZKV_PCR99_1 | 26.95 | 30 | ZKV_PCR99_1 |
| PCR with No beta-actin | | | | | | |
| LOD ($2 \times 10^{-5}$ dilution) | 36.79 | 30 | ZKV_PCR99_2_NoBa | 0 | 30 | ZKV_PCR99_2_NoBa |
| LOD ($2 \times 10^{-5}$ dilution) | 36.14 | 30 | ZKV_PCR99_2_NoBa | 0 | 30 | ZKV_PCR99_2_NoBa |
| LOD ($2 \times 10^{-5}$ dilution) | 36.85 | 30 | ZKV_PCR99_2_NoBa | 0 | 30 | ZKV_PCR99_2_NoBa |
| LOD ($2 \times 10^{-5}$ dilution) | 38.54 | 30 | ZKV_PCR99_2_NoBa | 0 | 30 | ZKV_PCR99_2_NoBa |
| LOD ($2 \times 10^{-5}$ dilution) | 38.46 | 30 | ZKV_PCR99_2_NoBa | 0 | 30 | ZKV_PCR99_2_NoBa |
| LOD ($2 \times 10^{-5}$ dilution) | 38.3 | 30 | ZKV_PCR99_2_NoBa | 0 | 30 | ZKV_PCR99_2_NoBa |
| LOD ($2 \times 10^{-5}$ dilution) | 36.96 | 30 | ZKV_PCR99_2_NoBa | 0 | 30 | ZKV_PCR99_2_NoBa |
| LOD ($2 \times 10^{-5}$ dilution) | 36.17 | 30 | ZKV_PCR99_2_NoBa | 0 | 30 | ZKV_PCR99_2_NoBa |

TABLE 17-continued

| | Zika NS5 | | | beta-actin mRNA | | |
|---|---|---|---|---|---|---|
| Concentration: ZKV RNA | [FAM] Ct | Threshold Value | Experiment # | [TET] Ct | Threshold Value | Experiment # |
| LOD ($2 \times 10^{-5}$ dilution) | 36.01 | 30 | ZKV_PCR99_2_NoBa | 0 | 30 | ZKV_PCR99_2_NoBa |
| LOD ($2 \times 10^{-5}$ dilution) | 36.27 | 30 | ZKV_PCR99_2_NoBa | 0 | 30 | ZKV_PCR99_2_NoBa |

Based on these studies using live Zika virus extracted for total nucleic acids (RNA/DNA) from human semen indicates that the LOD is 400 viruses/mL ($2 \times 10^{-5}$ dilution point) for the 91-bp amplicon.

Table 18 was generated from 3 studies using 'blinded' semen samples spiked with live virus of known titer. A variety of titers were used consistent with the level of virus found in naturally infected semen. Different technologists performed each of the experiments. Zika virus of known titers was added directly to whole human semen and extracted for total nucleic acid (RNA/DNA) and tested via multiplex RT-PCR using the described protocol. These assays are used to determine the consistency of the protocol using different personnel for detection of live Zika virus in human semen extracted for total nucleic acid (RNA/DNA). Negative semen samples are included. These reactions are multiplex RT-PCR including primer/probe sets for Zika and beta-actin mRNA (human positive internal control, IC). The stock concentration of live Zika virus was 200 million viral particles per mL; $2 \times 10^8$ virons/mL. This corresponds to $2 \times 10^6$ Plaque Forming Units (PFU, 100 virus particles generate 1 PFU for this strain). Twenty uL of live virus at each dilution point was added to 180 uL of whole semen and extracted according to protocol presented herein. Since 20 uL in 200 uL constituents a 1:10 dilution, the highest titer that can be tested in semen is $2 \times 10^7$ virons/mL. This added 1:10 dilution is incorporated into Table 18 below.

TABLE 18

| | Zika NS5 | | | beta-actin mRNA | | |
|---|---|---|---|---|---|---|
| Concentration: ZKV RNA | [FAM] Ct | Threshold Value | Experiment # | [TET] Ct | Threshold Value | Experiment # |
| Blind Test #1 | | | | | | |
| Semen 1_Negative | 0 | 30 | ZKV_PCR102A | 29.15 | 30 | ZKV_PCR102A |
| Semen 1_Negative | 0 | 30 | ZKV_PCR102A | 28.68 | 30 | ZKV_PCR102A |
| Semen 2_$5 \times 10^{-5}$ dilution | 34.08 | 30 | ZKV_PCR102A | 31.58 | 30 | ZKV_PCR102A |
| Semen 2_$5 \times 10^{-5}$ dilution | 34.86 | 30 | ZKV_PCR102A | 31.18 | 30 | ZKV_PCR102A |
| Semen 3_$10^{-1}$ dilution | 21.22 | 30 | ZKV_PCR102A | 0 | 30 | ZKV_PCR102A |
| Semen 3_$10^{-1}$ dilution | 21.12 | 30 | ZKV_PCR102A | 0 | 30 | ZKV_PCR102A |
| Semen 4_Negative | 0 | 30 | ZKV_PCR102A | 29.44 | 30 | ZKV_PCR102A |
| Semen 4_Negative | 0 | 30 | ZKV_PCR102A | 29.42 | 30 | ZKV_PCR102A |
| Semen 5_$10^{-4}$ dilution | 32.2 | 30 | ZKV_PCR102A | 28.96 | 30 | ZKV_PCR102A |
| Semen 5_$10^{-4}$ dilution | 31.58 | 30 | ZKV_PCR102A | 29.48 | 30 | ZKV_PCR102A |
| Semen 6_$10^{-2}$ dilution | 25.2 | 30 | ZKV_PCR102A | 30.57 | 30 | ZKV_PCR102A |
| Semen 6_$10^{-2}$ dilution | 24.76 | 30 | ZKV_PCR102A | 30.57 | 30 | ZKV_PCR102A |
| Semen 7_Negative | 0 | 30 | ZKV_PCR102A | 29.56 | 30 | ZKV_PCR102A |
| Semen 7_Negative | 0 | 30 | ZKV_PCR102A | 29.33 | 30 | ZKV_PCR102A |
| Semen 8_$10^{-3}$ dilution | 28.47 | 30 | ZKV_PCR102A | 30.56 | 30 | ZKV_PCR102A |
| Semen 8_$10^{-3}$ dilution | 28.3 | 30 | ZKV_PCR102A | 30.31 | 30 | ZKV_PCR102A |
| Blind Test #2 | | | | | | |
| Semen 1_$10^{-1}$ dilution | 21.25 | 30 | ZKV_PCR102B | 32.68 | 30 | ZKV_PCR102B |
| Semen 1_$10^{-1}$ dilution | 20.78 | 30 | ZKV_PCR102B | 31.75 | 30 | ZKV_PCR102B |
| Semen 2_Negative | 0 | 30 | ZKV_PCR102B | 29.4 | 30 | ZKV_PCR102B |
| Semen 2_Negative | 0 | 30 | ZKV_PCR102B | 29.69 | 30 | ZKV_PCR102B |
| Semen 3_$5 \times 10^{-5}$ dilution | 40.48 | 30 | ZKV_PCR102B | 32.35 | 30 | ZKV_PCR102B |
| Semen 3_$5 \times 10^{-5}$ dilution | 41.72 | 30 | ZKV_PCR102B | 32.32 | 30 | ZKV_PCR102B |
| Semen 4_Negative | 0 | 30 | ZKV_PCR102B | 27.33 | 30 | ZKV_PCR102B |
| Semen 4_Negative | 0 | 30 | ZKV_PCR102B | 27.7 | 30 | ZKV_PCR102B |

TABLE 18-continued

| | Zika NS5 | | | beta-actin mRNA | | |
|---|---|---|---|---|---|---|
| Concentration: ZKV RNA | [FAM] Ct | Threshold Value | Experiment # | [TET] Ct | Threshold Value | Experiment # |
| Semen 5_$10^{-3}$ dilution | 31.24 | 30 | ZKV_PCR102B | 32.15 | 30 | ZKV_PCR102B |
| Semen 5_$10^{-3}$ dilution | 31.01 | 30 | ZKV_PCR102B | 32.07 | 30 | ZKV_PCR102B |
| Semen 6_Negative | 0 | 30 | ZKV_PCR102B | 31.47 | 30 | ZKV_PCR102B |
| Semen 6_Negative | 0 | 30 | ZKV_PCR102B | 31.47 | 30 | ZKV_PCR102B |
| Semen 7_$10^{-4}$ dilution | 34.44 | 30 | ZKV_PCR102B | 31.45 | 30 | ZKV_PCR102B |
| Semen 7_$10^{-4}$ dilution | 34.66 | 30 | ZKV_PCR102B | 31.92 | 30 | ZKV_PCR102B |
| Semen 8_$10^{-2}$ dilution | 28.69 | 30 | ZKV_PCR102B | 32.49 | 30 | ZKV_PCR102B |
| Semen 8_$10^{-2}$ dilution | 28.41 | 30 | ZKV_PCR102B | 32.37 | 30 | ZKV_PCR102B |
| Blind Test #3 | | | | | | |
| Semen 1_$10^{-4}$ dilution | 0 | 30 | ZKV_PCR102C | 28.19 | 30 | ZKV_PCR102C |
| Semen 1_$10^{-4}$ dilution | 42.09 | 30 | ZKV_PCR102C | 27.83 | 30 | ZKV_PCR102C |
| Semen 2_$10^{-1}$ dilution | 24.87 | 30 | ZKV_PCR102C | 28.27 | 30 | ZKV_PCR102C |
| Semen 2_$10^{-1}$ dilution | 25.13 | 30 | ZKV_PCR102C | 28.95 | 30 | ZKV_PCR102C |
| Semen 3_Negative | 0 | 30 | ZKV_PCR102C | 27.87 | 30 | ZKV_PCR102C |
| Semen 3_Negative | 0 | 30 | ZKV_PCR102C | 28.21 | 30 | ZKV_PCR102C |
| Semen 4_$10^{-2}$ dilution | 26.21 | 30 | ZKV_PCR102C | 27.82 | 30 | ZKV_PCR102C |
| Semen 4_$10^{-2}$ dilution | 26.83 | 30 | ZKV_PCR102C | 28.47 | 30 | ZKV_PCR102C |
| Semen 5_Negative | 0 | 30 | ZKV_PCR102C | 27.56 | 30 | ZKV_PCR102C |
| Semen 5_Negative | 0 | 30 | ZKV_PCR102C | 28.12 | 30 | ZKV_PCR102C |
| Semen 6_$10^{-3}$ dilution | 27.51 | 30 | ZKV_PCR102C | 27.4 | 30 | ZKV_PCR102C |
| Semen 6_$10^{-3}$ dilution | 27.77 | 30 | ZKV_PCR102C | 27.31 | 30 | ZKV_PCR102C |
| Semen 7_$5 \times 10^{-5}$ dilution | 39.89 | 30 | ZKV_PCR102C | 27.31 | 30 | ZKV_PCR102C |
| Semen 7_$5 \times 10^{-5}$ dilution | 41.47 | 30 | ZKV_PCR102C | 27.66 | 30 | ZKV_PCR102C |
| Semen 8_Negative | 0 | 30 | ZKV_PCR102C | 27.54 | 30 | ZKV_PCR102C |
| Semen 8_Negative | 0 | 30 | ZKV_PCR102C | 27.8 | 30 | ZKV_PCR102C |

Based on these studies all end users scored 100% with respect to Zika detection in human semen. These studies show the detection of 200 virus particles per mL was detected in all samples at that titer even though the LOD based on prior studies is 400 virus/mL of semen.

It should be noted that both the 73-bp amplicon and the 91-bp amplicon can be used separately or in conjunction for confirmatory testing. In some embodiments, the 91-bp amplicon shows, to our surprise, increased sensitivity, with a Limit of Detection (LOD) of 400 viruses detected in 1 mL of semen sample. The 73-bp assay gave an LOD of 2000 viruses detected per mL. All the critical data was generated from Live Zika Virus, using the strain isolated in Puerto Rico in 2015/2016.

Example 4

Combinatorial Panel for Assaying Additional Pathogens

In addition to Zika virus, additional pathogens can also be tested simultaneously or separately in semen. In the field of reproductive medicine, it is of utmost importance to prevent the transmission of dangerous viral agents harbored by infected males and maintained in the male reproductive tract that can negatively impact female recipients and/or developing fetuses during pregnancy. High risk strains of human papillomavirus are the underlying cause of cervical cancers and several viruses of the Herpesvirus family can have serve consequences on fetal development, in particular, the fetal central nervous systems when infection is contracted at the time of conception via infected semen. One of the key weapons in the diagnostic armament are specialized testing protocols directed at the key biological material leading to female reproductive infections associated with sexual activity, as well as assisted reproductive technology; male semen. An amplification-based, multiplex assay has been developed to address this important clinical dilemma.

A combinatorial multiplex panel is outlined involving a single semen extract yielding full length DNA and RNA combined with RT-PCR and PCR components for detecting, respectively, Zika viral RNA and CMV, HPV 16 & 18, and HSV 1 & 2 viral DNA, including internal positive controls for patient derived DNA and RNA sequences to verify reaction integrity. The Qiagen Viral RNA mini kit, or a similar system, is utilized to extract and purify total nucleic acids from human specimen types This provides the genetic material for amplifying and detecting both RNA and DNA viruses for diagnostic purposes, including human genetic sequences, whether cellular mRNA or genomic DNA to serve as positive internal controls. Any standard 4-channel real-time thermocycler can be used for this combinatorial panel test.

As stated herein, up to 200-uL of whole, washed, or cryopreserved human semen is processed using an appropriate method such as Qiagen Viral RNA mini kit yielding intact total nucleic acid comprised of RNA and DNA. After collection of purified nucleic acid in nuclease-free elution buffer, a volume of the extract is used for an RT-PCR amplification assay for RNA genetic targets and a PCR amplification assay for DNA genetic targets as previously outlined. Since standard real-time thermocyclers in use in the industry are usually capable of 4-channel fluorescent detection, the PCR component of the panel involving 6 DNA targets must be performed in 2 separate tubes. Therefore, presently, one reaction tube is used for RT-PCR for the detection of Zika virus and the ACTB mRNA positive control, and two reaction tubes are used for PCR for detection of 1) HPV 16, CMV, and Amelogenin gene positive control; and 2) HPV 18, HSV 1, HSV 2, and Amelogenin gene positive control.

As an alternative panel design, the DNA PCR component can be performed in a single tube, instead of split into two reactions. In this design, the HPV portion of the assay which has two sub-types will be combined into a single fluorescence channel, such that detection of either type 16 or type 18 will generate the same signal. Likewise, HSV 1 & 2 can be combined into a single fluorescence channel, with detection of either type generating the same signal. In both cases, if a signal is generated in the HPV or HSV channels, the sample will be reflex tested using the individual probes for each sub-type to identify the sub-type underlying the HPV or HSV infection. In this design, a single RT-PCR tube contains Zika and ACTB primers and probes, and a single PCR tube contains primer and probes for HPV, CMV, HSV, and Amelogenin. The number of initial reactions is reduced from three tubes (RT-PCR and two PCR) to two tubes (RT-PCR and PCR) minimizing the number of manipulations and reducing overall workflow. Reflex testing to distinguish HPV or HSV subtypes would only be performed in the limited number of samples testing positive for either of these two DNA virus.

Additional, it is anticipated the next generation real-time fluorescence-based thermocyclers will increase the number of detection channels from 4 to 6, or more, expanding the multiplex capabilities and thus allowing the DNA PCR component of the semen test to detect all 6 DNA targets in a single reaction using unique flourochromes for each of the genetic targets: HPV 16, HPV 18, CMV, HSV 1, HSV 2, and Amelogenin gene internal positive control. Alternative designs to consolidate the combinatorial panel into the fewest number of steps, tubes, and manipulations can be considered.

In one embodiment, primers and probes used to detect CMV, HSV-1, HSV-2, HPV-16, HPV-18 as well as Amelogenin control are shown below:

Cytomegalovirus (CMV)

```
Forward:
                                           (SEQ ID NO: 10)
5'-CGG TGG CCA AAG TGT AGG-3'

Reverse:
                                           (SEQ ID NO: 11)
5'-AAG GTC TTT GCC CAG TAC ATT-3'

Probe:
                                           (SEQ ID NO: 12)
5'-Reporter-CTC ATC TGA CTC CTC GGC GAT GGC-
Quencher-3'
```

Herpes Simplex Virus Type 1 (HSV-1)

```
Forward:
                                           (SEQ ID NO: 13)
5'-ATA CCG ACC ACA CCG ACG AA-3'

Reverse:
                                           (SEQ ID NO: 14)
5'-ACG CAC CAC ACA AAA GAG ACC TT-3'

Probe:
                                           (SEQ ID NO: 15)
5'-Reporter-CTT CAG CGC GAA CGA CCA ACT AC-
Quencher-3'
```

Herpes Simplex Virus Type 2 (HSV-2)

```
Forward:
                                           (SEQ ID NO: 16)
5'-CGG GGT CGG TGT GGT GTT-3'

Reverse:
                                           (SEQ ID NO: 17)
5'-TGC CGT GAT ACG CGA TGC-3'

Probe:
                                           (SEQ ID NO: 18)
5'-Reporter-CGT TCG CAA TGC AGC TTA TGA CC-
Quencher-3'
```

Human Papillomavirus Type 16 (HPV-16)

```
Forward:
                                           (SEQ ID NO: 19)
5'-AGA ACC GGA CAG AGC CCA TTA CAA T-3'

Reverse:
                                           (SEQ ID NO: 20)
5'-TTC CTA GTG TGC CCA TTA ACA GGT CT-3'

Probe:
                                           (SEQ ID NO: 21)
5'-Reporter-ACG CTT CGG TTG TGC GTA CAA AGC ACA
CA-Quencher-3'
```

Human Papillomavirus Type 18 (HPV-18)

```
Forward:
                                           (SEQ ID NO: 22)
5'-CAA CAT AGC TGG GCA CTA TAG AGG C-3'

Reverse:
                                           (SEQ ID NO: 23)
5'-GAC ATA GAA GGT CAA CCG GAA TTT CAT TTT GG-3'

Probe:
                                           (SEQ ID NO: 24)
5'-Reporter-ACC GAG CAC GAC AGG AAC GAC TCC AAC-
Quencher-3'
```

Internal Positive DNA Control (Donor/Patient Derived) Gene Sequence (Amelogenin Gene):

```
Forward:
                                    (SEQ ID NO: 25)
5'-CCA GAG CAT AAG GCC ACC GGT AT-3'

Reverse:
                                    (SEQ ID NO: 26)
5'-ATC CAC CCA TGG GCT CGT AAC C-3'

Probe:
                                    (SEQ ID NO: 27)
5'-Reporter-TCA CCT GAG CCA ATG GTA AAC CTG-
Quencher-3'
```

In one embodiment, PCR conditions for the multiplex DNA PCR panel reaction setup is as follows:

Reagent Preparation—All stock regents are handled according to manufacturer's instructions with respect to storage, temperature, and expirations dates.

Primers/Probe set—Forward and Reverse primers and hydrolysis probes for each genetic target are maintained as 100 uM stock aliquots. Forward and Reverse primer stocks and hydrolysis probe stocks are mixed using appropriate volumes yielding a 10× mixture (see below) for each genetic target. This mixture is diluted 10-fold to final concentration of 1× during assay set-up using a preset Excel macro containing the proper dilution calculations based on the number of reactions and final assay volume.

DNA PCR reaction setup: Two reactions are performed in 25-uL volumes; PCRv1 and PCRv2. Each reaction is composed of the following primer/probe concentrations:
DNA PCRv1, HPV 16/CMV/Amelogenin:
  HPV 16 primers; 0.2 uM final concentration (range 0.1 to 0.4 mM) [2.0 mM, 10×]
  HPV 16 probe; 0.2 uM final concentration (range 0.1 to 0.4 mM) [2.0 mM, 10×]
  CMV primers; 0.2 uM final concentration (range 0.1 to 0.4 mM) [2.0 mM, 10×]
  CMV probe; 0.4 uM final concentration (range 0.2 to 0.8 mM) [4.0 mM, 10×]
  Amelogenin primers; 0.2 uM final concentration (range 0.1 to 0.4 mM) [2.0 mM, 10×]
  Amelogenin probe; 0.4 uM final concentration (range 0.2 to 0.8 mM) [4.0 mM, 10×]
PCRv1: HPV 18/CMV/Amelogenin reaction mix
  2.5 uL of 10×Taq Pol PCR buffer (Platinum Taq Polymerase, ThermoFisher Scientific)
  2.0 uL of $MgCl_2$ [50 mM] (final concentration; 4.0 mM)
  0.25 uL of nucleotide triphosphates (dNTPs) at [20 mM], 0.2 mM final concentrations
  2.5 uL of HPV 16 primers/probe [10×] (final concentration; 1×)
  2.5 uL of CMV primers/probe [10×] (final concentration; 1×)
  2.5 uL of Amelogenin primers/probe [10×] (final concentration; 1×)
  0.15 uL of Platinum Taq Pol Enzyme (ThermoFisher Scientific) at [5 U/uL] (final concentration; 0.03 U/uL, range 0.01 to 0.05 U/uL)
  7.6 uL sterile water
  5.0 uL template (extracted nucleic acids from clinical specimen)
  25.0 uL total volume
DNA PCRv2, HPV 18, HSV 1, HSV 2, Amelogenin:
  HPV 18 primers; 0.2 uM final concentration (range 0.1 to 0.4 mM) [2.0 mM, 10×]
  HPV 18 probe; 0.4 uM final concentration (range 0.2 to 0.8 mM) [4.0 mM, 10×]
  HSV 1 primers; 0.2 uM final concentration (range 0.1 to 0.4 mM) [2.0 mM, 10×]
  HSV 1 probe; 0.1 uM final concentration (range 0.08 to 0.2 mM) [1.0 mM, 10×]
  HSV 2 primers; 0.2 uM final concentration (range 0.1 to 0.4 mM) [2.0 mM, 10×]
  HSV 2 probe; 0.1 uM final concentration (range 0.08 to 0.2 mM) [1.0 mM, 10×]
  Amelogenin primers; 0.2 uM final concentration (range 0.1 to 0.4 mM) [2.0 mM, 10×]
  Amelogenin probe; 0.4 uM final concentration (range 0.2 to 0.8 mM) [4.0 mM, 10×]
PCRv2: HPV 18/HSV 1/HSV 2/Amelogenin Reaction Mix
  2.5 uL of 10×Taq Pol PCR buffer (Platinum Taq Polymerase, ThermoFisher Scientific)
  2.0 uL of $MgCl_2$ [50 mM] (final concentration; 4.0 mM)
  0.25 uL of nucleotide triphosphates (dNTPs) at [20 mM], 0.2 mM final concentrations
  2.5 uL of HPV 18 primers/probe [10×] (final concentration; 1×)
  2.5 uL of HSV 1 primers/probe [10×] (final concentration; 1×)
  2.5 uL of HSV 2 primers/probe [10×] (final concentration; 1×)
  2.5 uL of Amelogenin primers/probe [10×] (final concentration; 1×)
  0.15 uL of Platinum Taq Pol Enzyme (ThermoFisher Scientific) at [5 U/uL] (final concentration; 0.03 U/uL, range 0.01 to 0.05 U/uL)
  5.1 uL sterile water
  5.0 uL template (extracted nucleic acids from clinical specimen)
  25.0 uL total volume
Real-Time DNA PCR Thermocycler Profile for PCRv1 and PCRv2:
  Step 1: 2 min at 94° C.; 1×
  Step 2: 15 sec at 95° C.
  Step 3: 15 sec at 57° C.
  Step 4: 15 sec at 72° C.
  Repeat Steps 2-4, 44× (45 cycles total)
  Step 5: hold at 4° C.
Fluorochrome Dye Sets:
  PCRv1: HPV 16 (FAM)/CMV (Q760)/Amelogenin (TET)
  PCRv2: HPV 18 (Q760)/HSV 1 (FAM)/HSV 2 (CalRed)/Amelogenin (TET)

In one embodiment, 100-200 uL of whole, washed and/or cryopreserved semen is extracted with a lysis reagent yielding intact total nucleic acids (RNA/DNA). The isolated semen RNA/DNA is then subjected to two separate amplification reactions. One 4-color multiplex reaction utilizes RT-PCR to detect the presence of Zika viral RNA sequences as well as the presence of the ubiquitous human mRNA for beta-actin as a positive RNA internal control to verify assay performance. The patient/donor derived beta-actin mRNA must be visualized (scored) before any determination of Zika status is made. Failure to score the internal positive control (beta-actin mRNA) indicates a failed reaction.

The second 4-color multiplex reaction utilizes PCR to detect the presence of one or more of the following DNA viruses: cytomegalovirus (CMV), Herpes Simplex Virus (HSV) types 1 & 2, and/or Human Papillomavirus (HPV) high risk types 16 & 18. The reaction also includes detection of a gene sequence, Amelogenin X, derived from the patient/donor as a positive DNA internal control to verify assay performance. The patient/donor derived Amelogenin X gene sequence must be visualized (scored) before any determination of infection status is made. Failure to score the internal positive control (Amelogenin X) indicates a failed reaction.

In summary, the assay is a single sample, single extraction, 2-tube amplification reaction, potentially detecting, but not limited to, eight (8) sequence targets as indicated below:

In the event that signal is detected in those channels containing 2 targets, a positive result for a pathogen can be made. However, the extract is re-assayed using separate protocols for each of the possible targets to identify the pathogen yielding the original signal in that channel.

The protocol worksheets and data output for a routine run of eleven semen samples is summarized in Table 19 below.

TABLE 19

Real-time PCR for Zika, HPV 16, HPV 18, HSV-1, HSV-2, & CMV

| Specimen Type: Semen | Zika (FAM) | beta-actin (TET) | HPV 16 (FAM) | HPV 18 (Q670) | HSV-1 (FAM) | HSV-2 (CalRed) | CMV (Q670) | Amelogenin (TET) |
|---|---|---|---|---|---|---|---|---|
| Acc. # 54151 | 0 | 31.87 | 0 | 0 | 0 | 0 | 0 | 22.68 |
| Acc. # 54151 | 0 | 31.61 | 0 | 0 | 0 | 0 | 0 | 23.11 |
| Acc. # 54152 | 0 | 32.89 | 0 | 0 | 0 | 0 | 0 | 27.21 |
| Acc. # 54152 | 0 | 33.38 | 0 | 0 | 0 | 0 | 0 | 27.3 |
| Acc. # 54153 | 0 | 37.77 | 0 | 0 | 0 | 0 | 0 | 26.24 |
| Acc. # 54153 | 0 | 33.23 | 0 | 0 | 0 | 0 | 0 | 26.09 |
| Acc. # 54154 | 0 | 32.91 | 0 | 0 | 0 | 0 | 0 | 27.47 |
| Acc. # 54154 | 0 | 32.89 | 0 | 0 | 0 | 0 | 0 | 28.06 |
| Acc. # 54155 | 0 | 32.04 | 0 | 0 | 0 | 0 | 0 | 27.76 |
| Acc. # 54155 | 0 | 31.97 | 0 | 0 | 0 | 0 | 0 | 27.96 |
| Acc. # 54158 | 0 | 36.51 | 0 | 0 | 0 | 0 | 0 | 28.08 |
| Acc. # 54158 | 0 | 34.57 | 0 | 0 | 0 | 0 | 0 | 27.67 |
| Acc. # 54159 | 0 | 32.25 | 0 | 0 | 0 | 0 | 0 | 25.13 |
| Acc. # 54159 | 0 | 31.73 | 0 | 0 | 0 | 0 | 0 | 25.14 |
| Acc. # 54160 | 0 | 30.09 | 0 | 0 | 0 | 0 | 0 | 25.43 |
| Acc. # 54160 | 0 | 29.33 | 0 | 0 | 0 | 0 | 0 | 25.68 |
| Acc. # 54161 | 0 | 31.33 | 0 | 0 | 0 | 0 | 0 | 27.13 |
| Acc. # 54161 | 0 | 31.21 | 0 | 0 | 0 | 0 | 0 | 26.9 |
| Acc. # 54162 | 0 | 33.5 | 0 | 0 | 0 | 0 | 0 | 26.35 |
| Acc. # 54162 | 0 | 33.4 | 0 | 0 | 0 | 0 | 0 | 25.76 |
| Acc. # 54163 | 0 | 32.51 | 0 | 0 | 0 | 0 | 0 | 25.74 |
| Acc. # 54163 | 0 | 32.47 | 0 | 0 | 0 | 0 | 0 | 25.18 |
| Zika RNA | 31.15 | 0 | | | | | | |
| Zika RNA | 31.48 | 0 | | | | | | |
| Human RNA/DNA | 0 | 34.47 | | | | | | |
| No RNA/DNA | 0 | 0 | | | | | | |
| HPV 16 & 18 DNA, 10 genomes | | | 35.7 | 34.58 | 0 | 0 | 0 | 0 |
| HPV 16 & 18 DNA, 100 genomes | | | 30.63 | 28.94 | 0 | 0 | 0 | 0 |
| HSV 1 & 2 DNA, 10 genomes | | | 0 | 0 | 25.57 | 28.53 | 0 | 0 |
| HSV 1 & 2 DNA, 100 genomes | | | 0 | 0 | 22.2 | 25.35 | 0 | 0 |
| CMV DNA, 10 genomes | | | 0 | 0 | 0 | 0 | 28.16 | 0 |
| CMV DNA, 100 genomes | | | 0 | 0 | 0 | 0 | 24.51 | 0 |
| Human RNA/DNA | | | 0 | 0 | 0 | 0 | 0 | 27.34 |
| No RNA/DNA | | | 0 | 0 | 0 | 0 | 0 | 0 |

1) RT-PCR for RNA-based targets such as Zika virus RNA and beta-actin mRNA uses the flourochromes listed below.

| Zika detection | FAM channel (ex@ 450-495 nm) |
| Beta-actin mRNA | TET channel (ex@ 500-550 nm) |

2) PCR for DNA-based targets such as CMV, HSV 1 & 2, HPV 16 & 18 and Amelogenin X gene sequences uses the flourochromes listed below:

| HSV-1 and/or HPV 16 detection | FAM channel (ex@ 450-495 nm) |
| Amelogenin X detection | TET (ex@ 500-550 nm) |
| HSV-2 detection | TexRed channel (ex@ 565-590 nm) |
| CMV and/or HPV 18 detection | Q760 channel (ex@ 630-650 nm) |

Below is a summary of total semen samples tested to date as part of a research project screening healthy male semen donors. These donors gave complete medical histories including physical exams and underwent all FDA required infectious disease screening protocols. None of the donors visited or had contact with persons who traveled to Zika harboring countries or regions. This data set is used to establish specificity values. No samples of this donor population tested positive for Zika, HSV, or HPV. However, a single donor tested positive for CMV.

Zika testing only: 1,287 donors tested (all negative)

Zika plus CMV, HPV, HSV: 758 donors tested (one CMV positive)

The Zika assay is being used to test semen samples from males from Jamaica who may have had exposure to Zika through local mosquito populations. To date, one semen sample has tested positive for the Zika virus.

OTHER EMBODIMENTS

The examples have focused on specific primers and probes. Nevertheless, the key concept of detecting Zika in semen is, as one of ordinary skill in the art would understand, extensible to other primers and probes.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present disclosure provides among other things novel methods and systems for ZIKV detection. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

The invention claimed is:

1. A method for detecting Zika virus, comprising:
   (a) extracting nucleic acids from a human semen sample;
   (b) detecting a 73-nucleotide region in Zika virus non-structural protein 5 (NS5) mRNA using real-time reverse-transcription polymerase chain reaction (rRT-PCR), wherein said 73-nucleotide region consists of g.9389 to g.9461 of GenBank Accession number KU501215; and
   (c) simultaneously, in the rRT-PCR, detecting human beta-actin mRNA as positive control, comprising using a forward primer, a reverse primer and a TAQMAN® probe having the nucleic acid sequences of SEQ ID NOs: 7, 8 and 9, respectively, for detecting the human beta-actin mRNA.

2. The method of claim 1, wherein the nucleic acids are RNA.

3. The method of claim 1, wherein the human semen sample is fresh, refrigerated, frozen or cryopreserved.

4. The method of claim 1, wherein step (b) further comprises providing:
- a forward primer that is 15-25 nucleotides long and targets a region located within g.9389 to g.9414 of GenBank Accession number KU501215;
- a reverse primer that is 15-25 nucleotides long and targets a region located within g.9436 to g.9461 of GenBank Accession number KU501215; and
- a TAQMAN® probe that is 18-30 nucleotides long and targets a region located within g.9404 to g.9446 of GenBank Accession number KU501215.

5. The method of claim 4, wherein the forward primer, the reverse primer and the probe consist of the nucleic acid sequences of SEQ ID NOs: 1, 2 and 3, respectively.

6. A method for detecting two or more viruses, comprising:
- (a) extracting nucleic acids from a human semen sample;
- (b) subjecting a first portion of the nucleic acids to real-time reverse-transcription polymerase chain reaction (rRT-PCR) for detecting Zika virus nonstructural protein 5 (NS5) mRNA, while simultaneously, in the rRT-PCR, detecting human beta-actin mRNA as a first positive control; and
- (c) subjecting a second portion of the nucleic acids to real-time PCR for detecting one or more DNA viruses, while simultaneously, in the real-time PCR, detecting human Amelogenin gene as a second positive control.

7. The method of claim 6, wherein the nucleic acids are a mixture of RNA and DNA.

8. The method of claim 6, wherein step (b) comprises detecting a 73-nucleotide region from g.9389 to g.9461 or a 91-nucleotide region from g.9142 to g.9232 of GenBank Accession number KU501215.

9. The method of claim 8, further comprising providing:
- a forward primer that is 15-25 nucleotides long and targets a region located within g.9389 to g.9414 or g.9142 to g.9167 of GenBank Accession number KU501215;
- a reverse primer that is 15-25 nucleotides long and targets a region located within g.9436 to g.9461 or g.9207 to g.9232 of GenBank Accession number KU501215; and
- a TAQMAN® probe that is 18-30 nucleotides long and targets a region located within g.9404 to g.9446 or g.9157 to g.9217 of GenBank Accession number KU501215.

10. The method of claim 9, wherein the forward primer has the nucleic acid sequence of SEQ ID NO: 1 or 4, the reverse primer has the nucleic acid sequence of SEQ ID NO: 2 or 5, and the probe has the nucleic acid sequence of SEQ ID NO: 3 or 6.

11. The method of claim 6, wherein the one or more DNA viruses are selected from cytomegalovirus (CMV), herpes simplex virus (HSV) 1 & 2, and human papillomavirus (HPV) strains 16 & 18.

12. The method of claim 11, further comprising providing:
- a forward primer, a reverse primer and a TAQMAN® probe having the nucleic acid sequences of SEQ ID NOs: 10, 11 and 12, respectively, for detecting CMV;
- a forward primer, a reverse primer and a TAQMAN® probe having the nucleic acid sequences of SEQ ID NOs: 13, 14 and 15, respectively, for detecting HSV 1;
- a forward primer, a reverse primer and a TAQMAN® probe having the nucleic acid sequences of SEQ ID NOs: 16, 17 and 18, respectively, for detecting HSV 2;
- a forward primer, a reverse primer and a TAQMAN® probe having the nucleic acid sequences of SEQ ID NOs: 19, 20 and 21, respectively, for detecting HPV 16; and/or
- a forward primer, a reverse primer and a TAQMAN® probe having the nucleic acid sequences of SEQ ID NOs: 22, 23 and 24, respectively, for detecting HPV 18.

13. The method of claim 6, wherein step (c) comprises using a forward primer, a reverse primer and a TAQMAN® probe having the nucleic acid sequences of SEQ ID NOs: 25, 26 and 27, respectively, for detecting the human Amelogenin gene.

* * * * *